US008118772B2

(12) United States Patent
Dao et al.

(10) Patent No.: US 8,118,772 B2
(45) Date of Patent: Feb. 21, 2012

(54) BREAST PUMP DEVICE WITH SELF-CONTAINED BREAST MILK RESERVOIR

(76) Inventors: Stella Dao, Sacramento, CA (US); Dan Garbez, Sacramento, CA (US)

( * ) Notice: Subject to any disclaimer, the term of this patent is extended or adjusted under 35 U.S.C. 154(b) by 122 days.

(21) Appl. No.: 12/113,563

(22) Filed: May 1, 2008

(65) Prior Publication Data

US 2008/0208116 A1 Aug. 28, 2008

Related U.S. Application Data

(63) Continuation-in-part of application No. 11/104,776, filed on Apr. 12, 2005, now Pat. No. 7,559,915.

(60) Provisional application No. 60/618,685, filed on Oct. 13, 2004.

(51) Int. Cl.
*A61M 1/06* (2006.01)
*A61F 5/44* (2006.01)
*A61M 31/00* (2006.01)

(52) U.S. Cl. ............ 604/74; 604/346; 604/500

(58) Field of Classification Search ............ 604/74, 604/346
See application file for complete search history.

(56) References Cited

U.S. PATENT DOCUMENTS

| 155,720 | A | 10/1874 | Gray et al. |
| 684,078 | A | 10/1901 | Martin |
| 3,840,012 | A | 10/1974 | Rushton |
| 4,263,912 | A | 4/1981 | Adams |
| 4,270,538 | A * | 6/1981 | Murphy ............ 604/346 |
| 4,425,935 | A | 1/1984 | Gonzalez |

(Continued)

FOREIGN PATENT DOCUMENTS

GB 2138686 A 10/1984

OTHER PUBLICATIONS www.babybungalow.comwhisweardoub.html.

(Continued)

*Primary Examiner* — Nicholas Lucchesi
*Assistant Examiner* — Ian Holloway
(74) *Attorney, Agent, or Firm* — Howard B. Rockman

(57) ABSTRACT

The present invention is a compact and hands-free human breast milk collection device that fits into a mother's existing nursing or standard brassiere. The invention can be attached to a conventional electric or manual pump for active milk collection and also can be used without a pump for passive milk collection. Additionally, the invention can be used for collection of hand-expressed milk. The invention comprises a breast adaptor which, in an embodiment, has at one end a funnel-shaped inlet coupled to a reservoir, wherein when the breast is inserted into the breast adaptor, the breast milk is expressed into the reservoir through a unique valve assembly and the milk is stored in the reservoir until the device is removed and the collected milk emptied into a container. In an embodiment, the valve assembly is mounted concentrically on a second end of the breast adaptor. The valve assembly alternately opens and closes communication between the breast adaptor and the reservoir. The valve assembly further includes an overflow chamber and a baffle structure to prevent backflow of milk into the pump and associated vacuum or suction line. The invention, in an embodiment, also includes a unique connection apparatus that enables the vacuum hose of the disclosed breast milk collection device to be sealingly attached to a vacuum hose of varying sizes attached to a vacuum pump mechanism.

41 Claims, 19 Drawing Sheets

U.S. PATENT DOCUMENTS

| | | |
|---|---|---|
| 4,582,073 A | 4/1986 | Simkanich |
| 4,673,388 A | 6/1987 | Schlensog |
| 4,857,051 A | 8/1989 | Larsson |
| 4,892,517 A | 1/1990 | Yuan |
| 4,929,229 A | 5/1990 | Larsson |
| 5,009,638 A | 4/1991 | Riedweg |
| 5,071,403 A | 12/1991 | Larsson |
| 5,295,957 A | 3/1994 | Aida |
| 5,358,476 A | 10/1994 | Wilson |
| 5,571,084 A | 11/1996 | Palmer |
| 5,720,722 A | 2/1998 | Lockridge |
| 5,941,847 A | 8/1999 | Huber |
| 5,954,690 A | 9/1999 | Larsson |
| 6,379,327 B2 * | 4/2002 | Lundy ............... 604/74 |
| 7,223,255 B2 * | 5/2007 | Myers et al. ............ 604/74 |
| 2003/0167037 A1 | 9/2003 | Fialkoff |
| 2006/0111664 A1 * | 5/2006 | Samson et al. ............ 604/74 |

OTHER PUBLICATIONS www.easyexpressionproducts.com.
International Search Report dated Oct. 6, 2008.

* cited by examiner

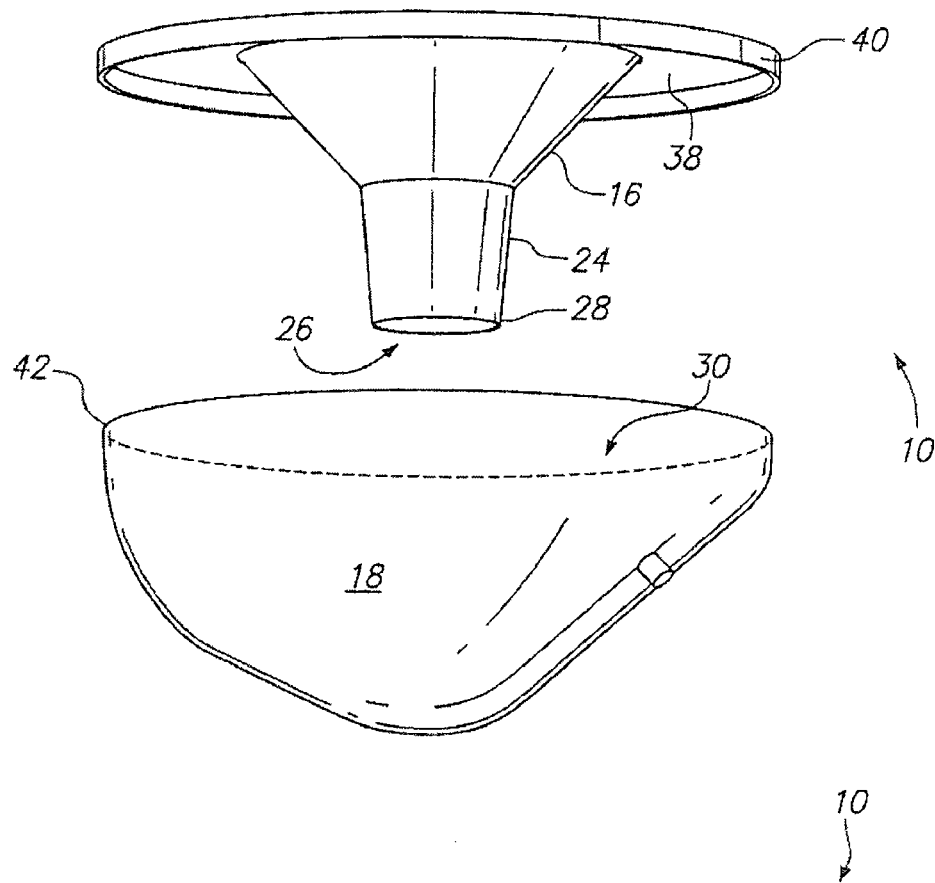
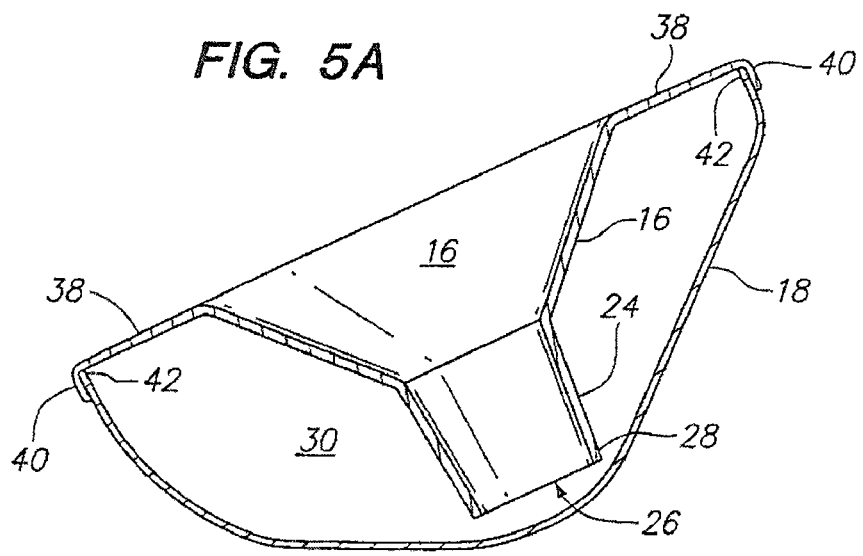

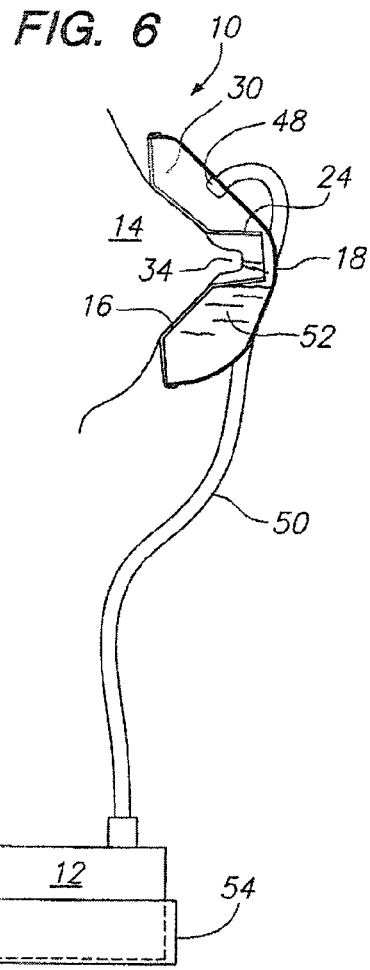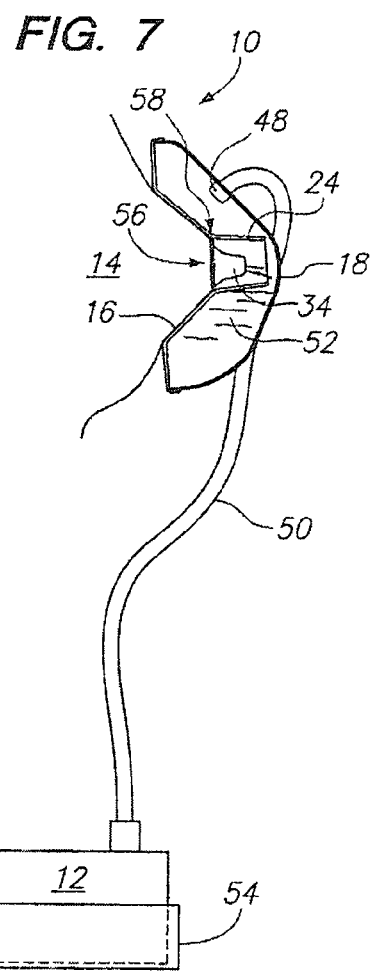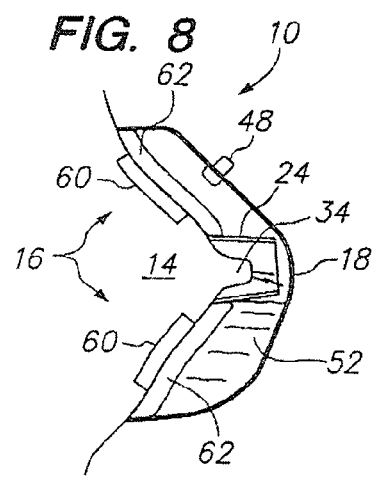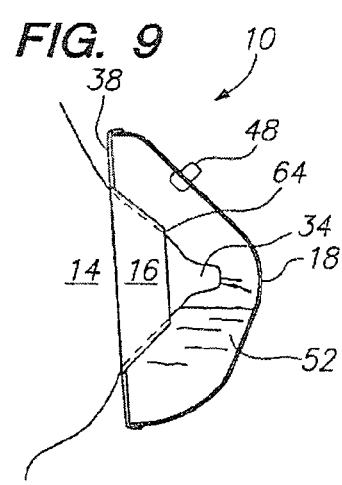

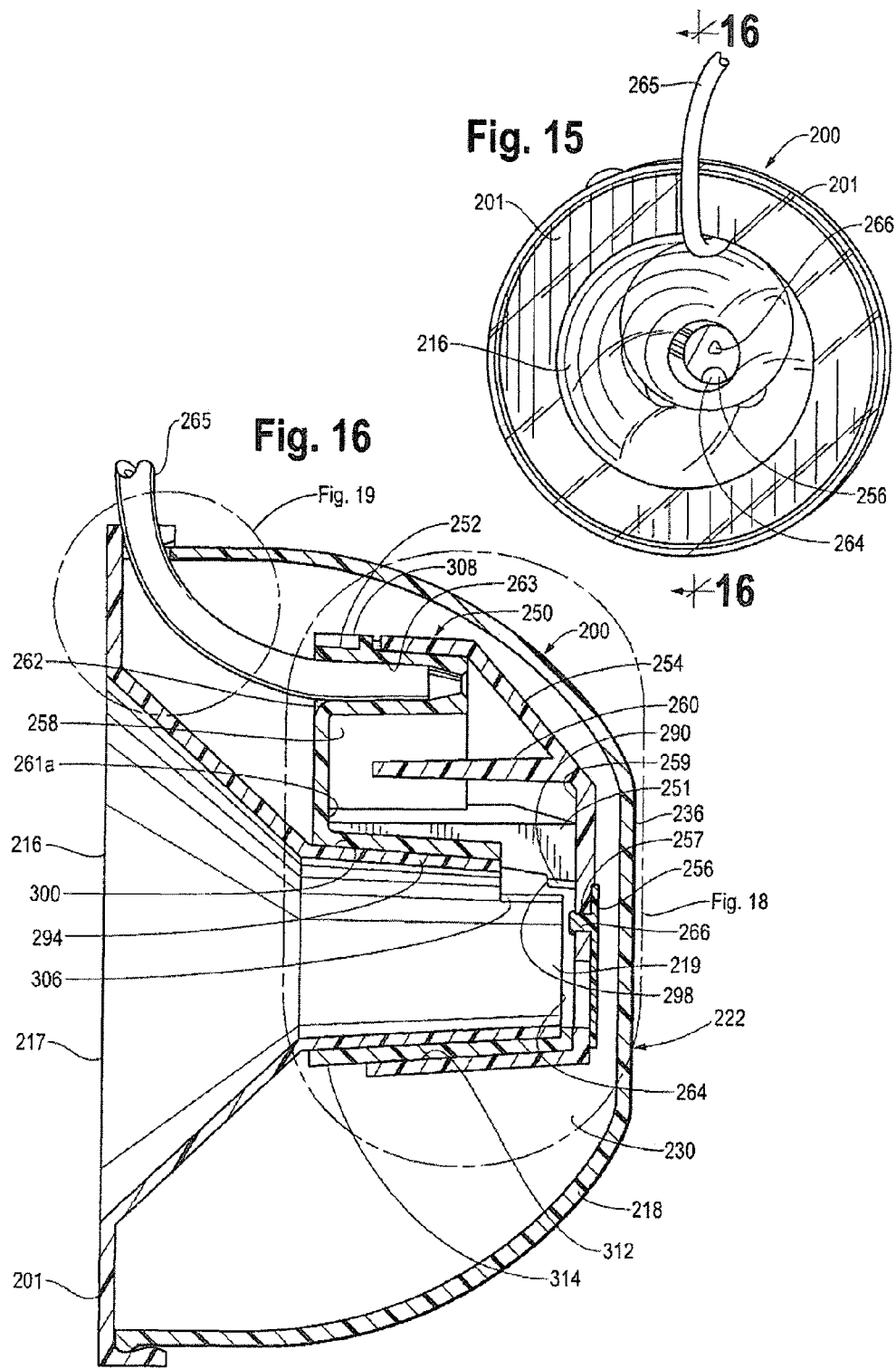

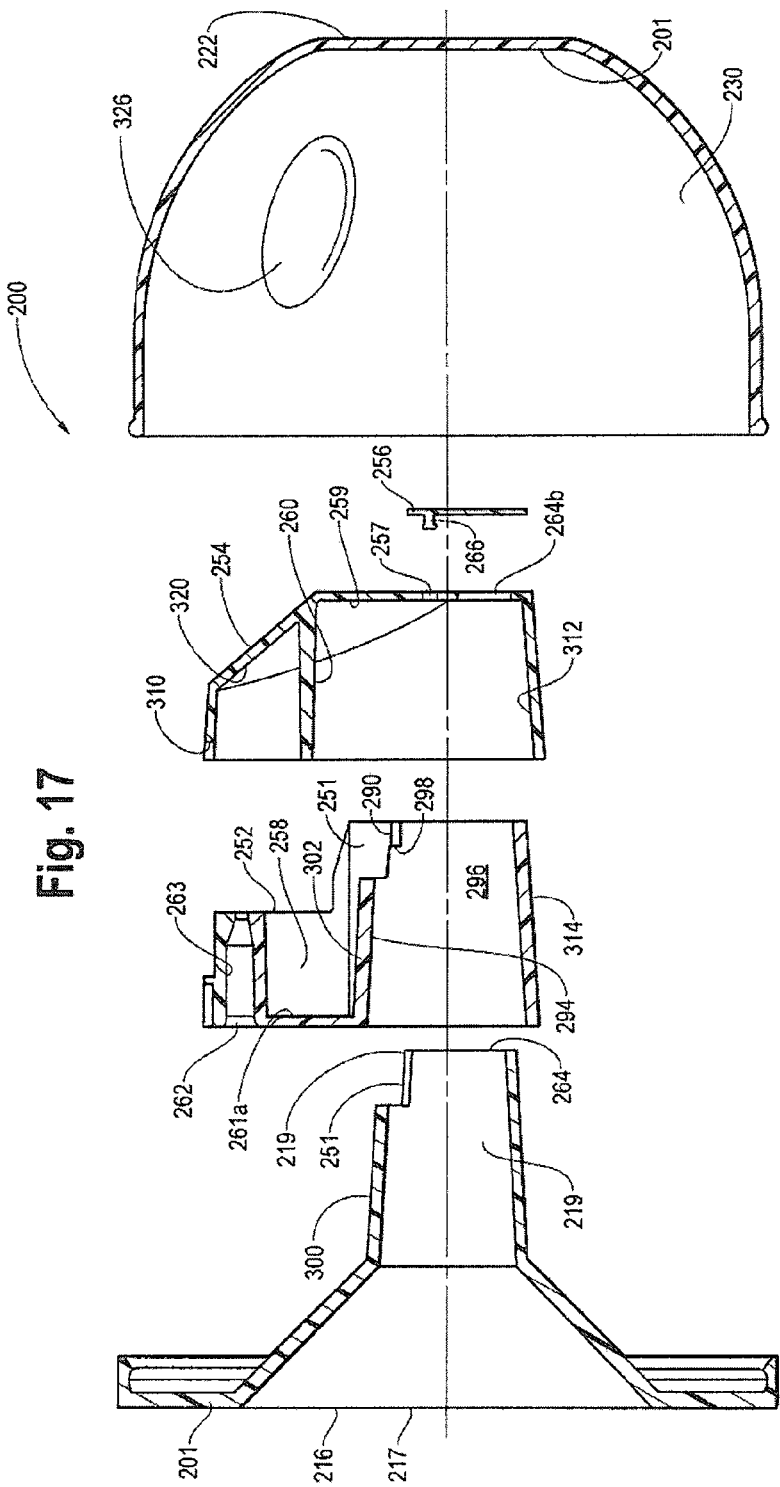

BREAST PUMP DEVICE WITH SELF-CONTAINED BREAST MILK RESERVOIR

CROSS REFERENCE TO RELATED APPLICATIONS

This utility patent application is a continuation-in-part of U.S. Nonprovisional application Ser. No. 11/104,776, filed on Apr. 12, 2005 now U.S. Pat. No. 7,559,915, which claims the benefit of U.S. Provisional Application Ser. No. 60/618,685 filed on Oct. 13, 2004, both of which are incorporated herein by reference to the extent allowed by law.

TECHNICAL FIELD

This invention relates to the field of human breast milk collection devices and more specifically, to breast milk collection devices which can fit discreetly and ergonomically within a woman's brassiere to provide hands-free breast milk collection, and can furnish breast milk to the collection device without causing milk to enter the associated vacuum pumping system, thus preventing backflow of milk into the vacuum pumping system.

BACKGROUND

Breastfeeding is recommended by the American Academy of Pediatrics, the World Health Organization and medical professionals worldwide as the preferred method for feeding infants during the first year of life. Human breast milk has significant health benefits that cannot be replicated by infant formula. Specifically, breast milk has been shown to reduce the incidence of infectious diarrhea, respiratory infections, otitis media and childhood obesity. Breastfeeding also has been shown to have health benefits for mothers, by reducing the risk of postpartum bleeding and anemia. Risks are also lowered for ovarian and premenopausal breast cancer. Further, postpartum weight loss is enhanced in breastfeeding mothers. Other benefits of breastfeeding include its comforting effect upon both mother and infant. For these reasons, many health professionals have determined that breastfeeding produces healthier, happier, infants and mothers, which is why breastfeeding is being promoted worldwide as a public health measure.

No infant formula can completely replicate the composition and benefits of human breast milk. Therefore, any proportion of breast milk in an infant's diet is preferable to no breast milk at all. Health professionals strive to encourage new mothers to provide their infants with the highest proportion of breast milk possible during the first year of life.

Unfortunately, there are many challenges to implementing breastfeeding. Breastfeeding requires constant attendance by the nursing mother every 1-2 hours, around the clock, for the baby's first 1-2 months of life, and approximately every 3-4 hours for the next 9 months of life. Furthermore, newborns may require up to 45 minutes per feeding. Nursing mothers must get adequate sleep, nutrition and hydration to maximize their milk production. For mothers with twins, triplets, or greater multiple births, the demand on the nursing mother's time is even greater. Some mothers have physical limitations which inhibit breastfeeding, such as inverted or sore nipples. Other mothers simply cannot make enough milk for their infants, and find that they must supplement their milk production with formula. In other cases, the physical limitations lie with the infant, namely premature or low birth weight infants who have weak suckling abilities, "floppy" infants with poor muscle tone, "tongue tied", cleft lip or cleft palate infants who cannot create a seal between their mouth and the nipple. In addition to physical limitations, societal norms create obstacles to breastfeeding. Breastfeeding in public is often prohibited, which limits mothers to breastfeeding at home.

Consequently, despite many government programs and initiatives to promote breastfeeding, most American women abandon breastfeeding long before the recommended first year of life. Studies have shown that only two-thirds of mothers breastfeed their infants when they leave the hospital, and at six months, that number shrinks to one third.

The alternatives to fulltime breastfeeding are either formula feeding, or feeding expressed human breast milk by bottle. Breast milk can be expressed, or released from the mother's lactating breasts, by massaging the breast by hand, or by the application of manual or electromechanical pumping equipment acting upon the breasts, both of which are commonly available in the domestic U.S. market.

For a woman to continue lactating a sufficient volume of milk, she must empty her breasts according to the feeding schedules and milk quantities demanded by an infant. Therefore, mothers who work outside of the home must stop working approximately every two and a half hours to pump breast milk in order to maintain an adequate milk supply. When pumping equipment is employed, it takes approximately 30 minutes for a mother to set up the pumping equipment, undress, pump, and perform cleanup. Because most current breast milk pumping and collection systems require a mother to frontally undress, a private setting is usually deemed necessary. This process, which must be continually repeated every two and a half hours is isolating, cumbersome, and extremely disruptive during work. Additionally, many breast pumping devices require the mother to use both of her hands to keep the equipment in position for efficient pumping, which prevents the mother from being able to perform other tasks as may be required in the workplace. The initial and recurring costs involved with using pumping equipment is a further factor which may limit the attractiveness of continuing to breastfeed.

Presently, few breast pumping devices allow for true hands-free operation. Most breast pump devices have hand-held funnel-shaped nipple adaptors, which allow suction to be applied to the nipples for milk expression. The nipple adaptors are then attached to baby bottles for milk collection. Examples of these types of devices are shown in U.S. Pat. Nos. 6,575,202 (Laford), 5,295,957 (Aida et al.), 5,071,403 (Larsson) and 5,358,476 (Wilson). Typically, suction is provided to these devices by a table-top electric pump. The pump can be situated nearby on the floor or on a tabletop, and the suction connection is made with small diameter (as little as 0.125" I.D.) flexible plastic tubing to facilitate the relatively low pressure, high volume, suction that is required to pull the woman's breast into the adaptor. A typical pump that is cylinder-actuated operates as a closed system, trapping a volume of air in the adaptor. When the woman's breast is pressed into the adaptor, it seals itself against the sides of the adaptor and forms the enclosed space in front of the nipple. When suction is applied, the malleable breast is pulled into the adaptor and toward the opening at the end of the funnel-shaped adaptor. A typical pump's cylinder, with an interior volume of several cubic inches, cycles back and forth repetitiously, completing an in-out "throw" over the course of a second or two, to create a massaging pulling rhythm upon the woman's breasts by alternating positive and negative pressure. This rhythm stimulates the mother's milk to be released, or "letdown," whereupon it flows, and is eventually collected in the manner already described.

Many of the vacuum source pumps are very durably constructed, provide significant suction, and since they are commonly used in hospital maternity wards to help new mothers stimulate milk production for their newborns, the pumps are constructed so that the major components can be disassembled and thoroughly cleaned between patients, for re-use. There are also a variety of other powered and manual pump types available on the market and well known in the pumping arts, ranging from very simple compact hand pumps, to innovative electromechanical concepts. The predominant and preferred pumps known to those skilled in the art for long term use are consumer versions of the very effective hospital grade pumps. For cost considerations, these pumps are not constructed to allow such thorough cleaning as the true hospital grade pumps, and so are intended for single users. However, since their performance characteristics are considered by professionals in the art of breastfeeding to be on a par with the pumps utilized in hospitals, these more substantial consumer pumps are commonly referred to as "hospital grade."

Certain pumps utilize an electromechanical construction with an impeller or other means that creates a constant suction with a pressure relief mechanism or valve, wherein the pump builds up negative pressure to some predefined, preset or adjustable maximum, and then a relief valve or other means releases the negative pressure, so that during the cycle the vacuum pressure peaks, then is relieved and suction drops and approaches a more close-to-neutral negative pressure measurement. In these constant suction pumps, the negative pressure builds up, is relieved, and then the cycle repeats itself as the relief mechanism shuts itself off again and negative pressure begins to build up again.

In these constant suction systems, the tendency for milk to migrate through the vacuum lines is great, and a key element often utilized to protect the pump's works from contamination is an inline porous filter in the vacuum feed line, which is well known in the art. These filters allow air to pass through, but collect most or all of the milk that reaches them. These filters can then be regularly cleaned or replaced when they have collected too much milk, allowing adequate air passage to achieve the desired suction. These pumps can be cost effective and efficient pumps for users who must pump frequently.

Many pumps during a typical cycle create negative pressure, and then alternately return toward a neutral pressure, which may give the user the sense of an alternating negative and positive pressure, even though no positive pressure may actually be measured during the majority of cycles from the pump. The benefit of these systems is that the adaptor, once placed against the breast, has a tendency to hold onto the breast, especially if the pump's cycle, once engaged and some air is purged from the trapped enclosure, alternates between strong negative pressure and weak negative pressure, but never alternates to all the way back to a neutral or positive pressure. If substantial positive pressure was actually introduced into this cycle, there would be a tendency to "blow" the adaptor off the breast, resulting in a disruption of the pumping rhythm, and possibly causing small amounts of milk in the adaptor to leak from the device and onto the user, rather than migrate into the collection container. For these reasons, during the initial engagement of the pumping cycle and the purging of excess air from the enclosure, and for the duration of the pumping session, a secure seating of the adaptors to the breasts is preferred, to establish a consistent and relaxing rhythm which most mothers find essential to letting down their milk, which does not usually come for a minute or more after the pumping has begun. Thus, even though a pump, once engaged for a pumping session may never reach into the positive pressure range on an atmospheric scale, the valving means adapted for such pumps are usually weak enough so that simply the weight of expressed milk which builds up within the enclosure can force itself through.

For alternating cycle pumps, some combination of valving and relief features are especially important to allow the volume of air trapped in the enclosure to constantly adjust itself, as the propensity for a malfunction to cause the adaptor to "blow" off the breast is more common with these pump types. What is common to all pumps, however, is that they of necessity, to stimulate the mother to release milk somewhat replicate the suckling of an infant, and so the sensation that must be created by the pump alternates between a somewhat strong negative pressure, and a weak or non-existent negative pressure, with a complete alternating cycle usually lasting only a second or two. These various pump systems, during a single cycle, alternate between generating a stronger negative pressure until a peak, and then the mechanism begins to cycle in the other, or "positive," direction, by whatever mechanical means, thereby relieving negative pressure within the subject enclosure. In this context, "positive pressure" does not necessarily refer to an objective measure of pressure within the device, relative to the surrounding atmospheric pressure.

Different pumps have different cycling characteristics, and differ from one another in achievable pressures. Different users may differ in their preferences for the specific rhythmic characteristics of various pumps on the market, but those skilled in the art generally agree that the more substantial "hospital grade" pumping equipment that provides more negative pressure and a more reliable and consistent suction and rhythm provides the most benefit for mothers whose circumstances require that they must for an extended period frequently utilize a breast pump. While many of these devices provide good suction and milk collection characteristics, hands-free operation is not possible because of the need to use the hands to hold the device against the breast during milk collection. Furthermore, because of the size and shape of these devices, the user must be frontally undressed to pump milk.

Some manufacturers have attempted to make pumping more discreet and hands-free by securing the assembly of adaptors, bottles and hoses with specialized straps, brassieres and harnesses. These types of devices are represented in U.S. Pat. Nos. 6,004,186 (Penny) and 6,379,327 (Lundy). However, since the entire assembly of adaptors, bottles and hoses is relatively large and cumbersome, in practice these devices still require a woman to undress to put on and to remove these devices with each use. Furthermore, as the bottles fill with milk, they may require some support of the bottle assembly system by hand.

U.S. Pat. No. 6,440,100 (Prentiss) presents a hands-free option which uses a low profile nipple cap held in place by a nursing brassiere. The nipple cap is placed over the nipple and a tube, for both vacuum supply and milk collection, extends from below the nipple cap to a collection container. A vacuum source, such as an electric pump, draws the milk from both breasts into the collection container which hangs below the brassiere. While this solution goes a long way towards providing a hands-free design, the placement of the collection container outside of the brassiere is cumbersome and unwieldy when placing and removing this device.

Also, while Prentiss attempts to provide an unobservable and virtually unnoticeable low profile application beneath normal clothing, the Prentiss design raises other issues.

Namely, Prentiss attempts to minimize the profile of the nipple cap by placing the vacuum source directly below the nipple. With this design, when suction is applied, the nipple is drawn downward, which tends to inhibit the flow and expression of milk by drawing the nipple onto the vacuum source or by pinching the milk ducts. Ideally, the nipple should be drawn forward to create the smooth and unobstructed action necessary to trigger the expression of milk. Elongation of the nipple and forward suction is the same as that applied by a suckling infant. Therefore, while Prentiss is likely to be effective for passive milk collection or for women with an abundant milk supply who require little suction to release their milk, its design may result in the failure to trigger the milk expression reflex in many women.

A hands-free pump is manufactured by Whisper Wear, Inc., of Marietta Ga. This device is comprised of a dome-shaped body having a self-contained AA battery powered pump. The rear of the body has a funnel adaptor for placement of the nipple. This device is only several inches in diameter and can be placed easily and discreetly within a regular brassiere. A collection bag attaches to the device and visibly hangs below the brassiere. If two devices are used at once, two bags are necessary for milk collection. While less cumbersome and completely portable when compared to the other solutions discussed herein, the use of the hanging plastic milk bags employed by the Whisper Wear device is unwieldy. Additionally, the system is expensive when the up front costs of the device are considered along with the ongoing costs of disposable batteries and single-use collection bags. This renders the system uneconomical for many mothers. But perhaps the greatest shortcoming of the Whisper Wear device when compared to the larger tabletop electric pumps is the strength of the suction it applies to the breast. The problem is one of scale. Once the Whisper Wear pump is placed over the nipple, the total volume of air trapped inside the mechanism is quite small, usually less than one cubic inch on average. Furthermore, the housing of the device limits the "throw" within this cavity to less than an inch, resulting in a much lower displacement, and therefore, a much less vigorous pumping action for milk expression. Also, being an integrated mechanical pump and battery, coupled with the weight of a suspended milk reservoir, the Whisper Wear devices are much heavier when worn hands-free within a brassiere than the adaptor and bottle assemblies discussed previously, which use tabletop electric pumps. During use, the weight and placement of the Whisper Wear devices within the bra can pinch some milk ducts, while simultaneously emptying others. These characteristics make the Whisper Wear pump inadequate for many women as a full time pumping solution. A stronger pump is necessary for some women to relieve obstructed milk ducts and empty their breasts completely.

U.S. Pat. No. 4,857,051 to Larsson ("Larsson") discloses a breast pump device having a hood member with a first funnel end and a second end which communicates with a collection chamber and a vacuum line. Larsson further discloses a breast pump device having a valve mechanism which closes a collection chamber when a vacuum is applied to a hood member and which opens the collection chamber when the vacuum is removed. Larsson further discloses a baffle in the hood member where the baffle is formed by a separation wall located between the second end of the hood member and the vacuum line. The baffle is located directly in front of a user's nipple when her breast is placed against the hood member in use of the pump device and prevents milk from reaching the vacuum line. Larsson does not disclose a breast pump collection device having a breast adaptor with a valve assembly wherein the valve assembly comprises a baffle structure configured to prevent the back flow of milk into the vacuum line when large amounts of aerated milk flow up into an overflow chamber before the suction of a negative pumping cycle is released, without milk entering the vacuum line.

U.S. Pat. No. 4,929,229 to Larsson ("Larsson") discloses another breast pump device having a hood member with a first funnel end and a second end which communicates with a collection chamber and a vacuum line. A downwardly extending separation wall forms a baffle located between the second end of the hood member and the vacuum line. Milk that is expressed into the hood member is then blocked by the separation wall or baffle from reaching the vacuum passage. Again, this baffle is located directly in front of a user's nipple when her breast is placed against the breast shield assembly and prevents milk from reaching the vacuum passage. Larsson here does not disclose a breast pump collection device having a breast adaptor with a valve assembly wherein the valve assembly comprises a baffle structure configured to prevent the back flow of milk into the vacuum line when large amounts of aerated milk flow up into an overflow chamber before the suction of a negative pumping cycle is released.

U.S. Pat. No. 6,652,484 to Hunckler, et al. ("Hunckler") discloses a breast pump device having a downwardly extending separation wall forming a baffle located between a second end of a breast hood or breast shield assembly and a vacuum passage. Milk that is expressed into the breast shield assembly is then blocked by the separation wall or baffle structure from reaching the vacuum passage. Again, this baffle is located directly in front of a user's nipple when her breast is placed against the breast shield assembly and prevents milk from reaching the vacuum passage. Hunckler does not disclose a breast pump collection device having a breast adaptor with a valve assembly wherein the valve assembly comprises a baffle structure configured to prevent the back flow of milk into the vacuum line when large amounts of aerated milk flow up into an overflow chamber before the suction of a negative pumping cycle is released.

Therefore, it would be desirable to have a pumping system that is hands free, but that is also easy to assemble, disassemble and clean, and reassemble, and to position under normal clothing without the need to undress or to don complicated and overtly visible harness systems, which pumping system can be adapted to function with a wide variety of the more substantial "hospital grade" pump technologies available.

Passive milk collection is also an area of breastfeeding worth addressing. Passive milk collection extends from the natural "letdown" reflex a woman experiences when an infant "latches" onto a woman's breast and begins nursing. When a breast is stimulated to release milk by a nursing infant, or through pumping a single breast, the second breast also naturally begins to release milk. If the milk being expressed from the second, unattended breast is not collected, the amount of milk that is wasted can range from a negligible percentage to as much as a third of a mother's milk supply. Therefore, due to this "letdown phenomenon," a great deal of milk that could be collected and fed to the infant via bottle is currently being wasted by most breastfeeding mothers. Presently, the predominant practice among nursing mothers to address this phenomenon is the use of absorbent, disposable or reusable pads placed inside the bra cup of the unattended breast.

Therefore, it would be desirable to have a device that can collect passively released milk from the unattended breast for subsequent feeding.

Breastfeeding physically challenged infants presents its own special problems. A significant number of infants with physical challenges, such as floppy infants, premature infants, or infants with cleft lip/palate have difficulty initiating the letdown reflex on their own. These challenges may be due to a lack of adequate strength to latch onto the breast, difficulty creating sufficient suction, or a lack of focused attention. As a result, many physically challenged infants cannot derive sufficient caloric intake for their sustenance from natural breast feeding. It would therefore be desirable to have a compact, hands-free device which can be used to pump one breast, thereby initiating the letdown reflex from both breasts, for the purpose of allowing a mother to hold and nurse a physically challenged infant from the opposite breast.

Consequently, a need exists for a breast milk collection device which can fit completely within a woman's standard brassiere. Such a device would be less likely to interfere with breastfeeding from the opposite breast and avoid the isolating, disruptive, and sometimes embarrassing need to disrobe to pump breast milk, which device can be adapted to function with a wide variety of the more substantial "hospital grade" and other pump technologies available.

A need also exists for a breast milk collection device that is both sufficiently powerful and hands-free.

A further need exists for a breast milk collection device that provides a viable solution for passive milk collection while simultaneously breastfeeding.

A need also exists for a breast milk pumping and collection device which can help compromised infants breastfeed.

Furthermore, a need exists for a breast milk collection device having reduced maintenance requirements provided by inhibiting the back flow of breast milk into the pump or suction lines.

A further need exists for a breast milk collection device having a vacuum pressure hose inlet port that is located apart from the path of milk expressed from the breast during the pumping operation, whereby the inlet port is not in direct contact with the expressed milk.

An additional need exists for a breast milk collection device having an overflow chamber and baffle combination that when the flow of breast milk is large in a single cycle, milk flows into the overflow chamber from a drip tube at an end of the breast adaptor before suction is released. When the overflow chamber is used, the mixture of milk and air in the drip tube can cause turbulence in the liquid, causing the milk to bubble and become airborne due to the suction force. The baffle in the overflow chamber deflects or redirects any airborne mist of milk that is pulled in the direction of the vacuum hose inlet port. In this way, bacteria-forming milk is kept from entering the pump's inner works and suction hoses.

A need also exists for a hands free, concealable and ergonomically shaped breast milk collection device that can be adapted for use with an internal or inline filter system for use with a constant suction pump, so that air is allowed to pass through the filter, while milk is trapped, protecting the pump's inner works.

A further need exists for a hands free, concealable and ergonomically shaped breast milk collection device that can be supported by an ordinary bra, which also integrates a vacuum barrier, to allow use of the device with pumps that require separation of the air in the vacuum lines and pump works from the air in direct communication with the breast and milk collection means.

Yet another need exists for a breast milk collection device whose several parts are easily manually disassembled for cleaning and decontamination, and are subsequently easy to manually reassemble in only a single, correct configuration for proper use of the collection device.

A further need exists for a hands free, concealable and ergonomically shaped breast milk collection device wherein a tortuous path is provided between the application of suction pressure and the breast for the purpose of preventing the backflow of expressed milk into the suction pressure hose or related suction pump mechanism.

Still another need exists for a breast milk collection device having an adaptor connected between the collection device vacuum hose and the outlet hose of a vacuum pump system that allows the vacuum hose and the outlet hoses to be properly connected even where the two hoses have different inner or outer diameters.

Yet another need exists for a breast milk collection device having a source of vacuum pressure applied to the breast to produce the expressions of breast milk, wherein the source of vacuum pressure is totally isolated from the flow path of the milk from the breast into the collection device reservoir.

The foregoing reflects the state of the art of which the inventors are aware, and is tendered with a view toward discharging in part the inventors' acknowledged duty of candor, which may be pertinent to the patentability of the present invention. It is respectfully stipulated, however, that the foregoing discussion does not teach or render obvious, singly or when considered in combination, the inventors' claimed invention.

SUMMARY OF THE INVENTION

The present invention is a compact, ergonomic and hands-free human breast milk collection device that fits into a mother's existing nursing or standard brassiere. The invention can be attached to a regular electric pump or manual pump utilizing suction hoses for active milk collection, and also can be used without a pump for passive milk collection and to collect manually expressed breast milk.

The invention comprises a breast adaptor which is preferably a funnel-shaped inlet coupled to a reservoir, wherein when the breast is inserted into the breast adaptor, the expressed breast milk flows, or drips into the reservoir. In an embodiment, a flap valve may be inserted between the drip tube and the reservoir. The milk is held in the reservoir until the device is removed and emptied. In the illustrated embodiment, the reservoir takes the form of a cup, and the breast adaptor takes the form of a funnel within a lid, which adaptor detachably couples upon the open end of the reservoir cup. The reservoir can also be formed into the shape of a woman's breast, thereby providing a more natural appearance when the device is placed into a woman's brassiere. In another embodiment, the invention further comprises a valve assembly mounted concentrically on a second end of the breast adaptor. The valve assembly alternately opens and closes communication between the breast adaptor and the reservoir. The valve assembly comprises a valve body, a valve cap mounted concentrically on the valve body, and a valve flap attached to the valve cap. The valve assembly further includes a baffle structure integrally formed with an interior wall of the valve cap and extending substantially into an overflow chamber, to prevent the overflow of milk into the pump and associated vacuum lines before suction is released from a negative pressure cycle of the pump.

Another embodiment of the invention eliminates the baffle structure and fills much of the overflow assembly with a barrier comprising collapsible bladder whose internal volume is in direct communication with the assembly's vacuum hose port, and which barrier largely conforms to the interior surface of the overflow chamber when not subjected to negative pressure. When vacuum pressure is exerted into the collapsible bladder within the relatively more rigid overflow chamber, the bladder collapses in the direction of the vacuum inlet, and the negative pressure is communicated to the rest of the enclosure of the overflow chamber and the adaptor, directly applying the negative force on the breast, and ultimately inducing milk letdown, as has been described.

Yet another embodiment of the invention may provide a filtration material, as commonly known in the art, between the overflow chamber and the vacuum passage for use with a constant suction pump, allowing the collection device to be utilized with these economical devices while protecting their mechanical works.

BRIEF DESCRIPTION OF THE DRAWINGS

The invention will be more fully understood by reference to the following drawings which are for illustrative purposes only:

FIG. 4 is an exploded perspective view of the inventive device of FIG. 1 showing the reservoir being detachable from the adaptor.

FIG. 5A is a side cutaway view of the inventive device of FIG. 1.

FIG. 6 is a close up cutaway side view of the inventive device of FIG. 1 shown attached to a woman's breast and coupled to an electric pump device.

FIG. 7 is a close up cutaway side view of the inventive device of FIG. 1 shown attached to a breast and coupled to an electric pump device. This view also includes a milk barrier located in the breast adaptor to prevent the back flow of milk.

FIG. 8 is a close up cutaway side view of the inventive device of FIG. 1 which employs an air or fluid filled bladder for enhanced comfort and sealing characteristics.

FIG. 9 is a close up cutaway side view of the inventive device of FIG. 1, this view eliminating the drip tube to enhance the device's usefulness for passive breast milk collection.

FIG. 15 is a rear perspective assembly view of another alternative embodiment of the inventive device.

FIG. 16 is a side sectional assembly view of the embodiment of the inventive device shown in FIG. 15 taken along line 16-16 in FIG. 15.

FIG. 17 is an exploded side sectional view of the illustrated embodiment of the inventive device of FIGS. 15 and 16.

DETAILED DESCRIPTION OF THE PREFERRED EMBODIMENTS

The inventive device dramatically improves the feasibility of pumping breast milk for women by allowing for the use of a breast pump at a stationary place in the workplace, in a vehicle with a power adaptor, or other public places with a minimum of interference or immodesty, and relatively minor disruption in these settings compared with the current state of the art for mothers who pump breast milk. Also, by eliminating the pump, the present invention can function as a passive breast milk collection device.

Figure 1:
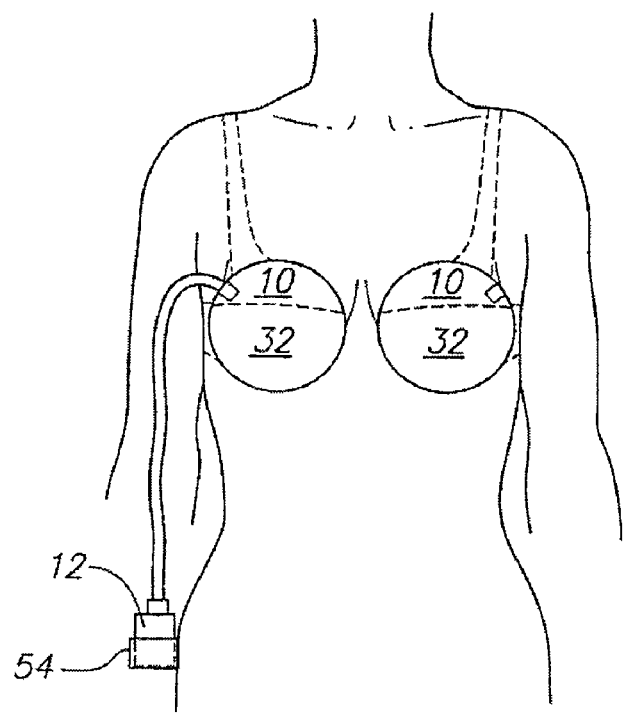
FIG. 1 is a front perspective view of a woman's torso showing an embodiment of the inventive device attached to each breast for completing a breast pumping cycle.
Figure 2:
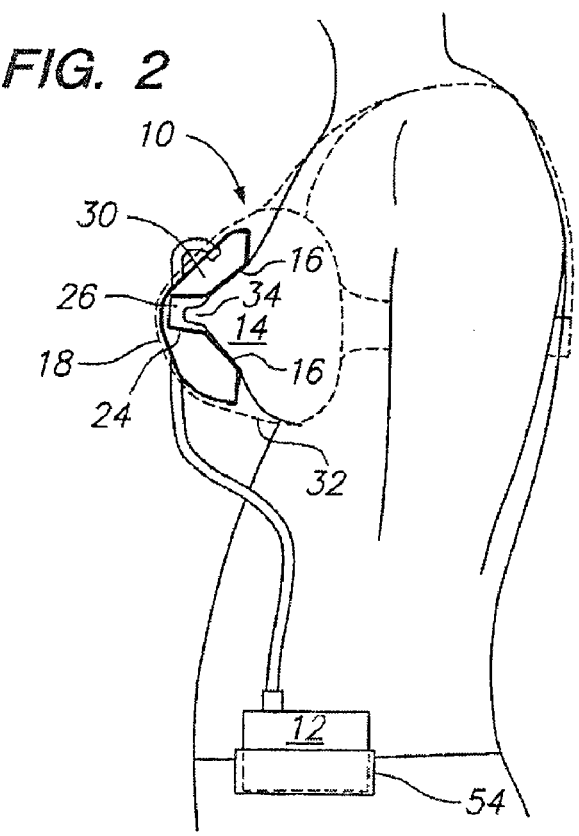
FIG. 2 is a side view of a woman's torso showing the inventive device of FIG. 1 being positioned in a brassiere for hands-free breast milk collection.

Referring to FIGS. 1 and 2, the inventive device 10 is shown attached to a woman's breast with a pump 12 attached in a typical breast milk collection mode. As shown, the device 10 includes an adaptor 16 within which the breast 14 is inserted, the adaptor 16 opening into a reservoir 18 which collects breast milk being expressed from the breast 14. The adaptor 16 includes a funnel, which is a shape that has been found to accommodate a wide variety of breast shapes and sizes. Additionally, the adaptor 16 and reservoir 18 can be made in various larger or smaller dimensions to accommodate larger or smaller breasts.

Referring also to the additional figures, the wide end of the funnel-shaped adaptor 16 opens to the rear 20 of the device 10. Proceeding forward from the rear 20 to the front 22 of the device 10, the adaptor 16 narrows and terminates at a drip tube 24 having an aperture 26 at its distal end 28, through which flows expressed breast milk to fill the reservoir 18. The funnel adaptor 16 protrudes a distance into the confines of the reservoir's interior volume 30 to give the device 10 a compact configuration. Also, the protrusion of the adaptor 16 into the reservoir 18, which can be an inch or more, gives the nipple room to elongate in a forwardly driven motion during pumping, which provides an optimal nipple orientation for milk expression. This orientation avoids pinching off of milk ducts which can lead to reduced milk expression. As shown in FIG. 2, a large portion of the breast 14 fits into the adaptor 16 and the compact configuration of the device 10 further aids in its ability to fit discreetly within a woman's standard or nursing brassiere 32. The fact that the reservoir 18 fits into a brassiere cup 32 obviates the need to have external collection bags or bottles located outside of the brassiere cup. In this way, the adaptor 16 and reservoir 18 comprise a single self-contained unit that is not dependent on external collection containers. The device 10 is shown placed within a woman's brassiere 32, in position for either pumping milk or passive milk collection. The profile of the device 10 is such that it does not protrude extensively beyond that of a normal woman's breast profile and may give the user the appearance of wearing a figure enhancing brassiere.

The adaptor 16 is preferably formed from a variety of materials including polypropylene, silicone or materials which may be developed in the future capable of making a superior seal around the breast 14 (to reduce leakage of expressed breast milk) or by making the adaptor 16 more breathable or more comfortable to wear. The materials or combination thereof can be made to be firm or soft, slick or sticky. For example, a sticky silicone might be used to form the adaptor 16 so that a tight fitting seal is made with the breast 14 while the reservoir 18 might be comprised of a rigid plastic. The rigid reservoir 18 could be formed in a shape to match that of a natural breast profile. Alternatively, the adaptor 16 and reservoir 18 might be made of a more flexible material to assume a natural breast profile as it conforms to a brassiere cup, while the drip tube 24 remains rigid to provide a closed chamber around the nipple 34 that will not collapse under the force of negative suction.

Figure 3A:
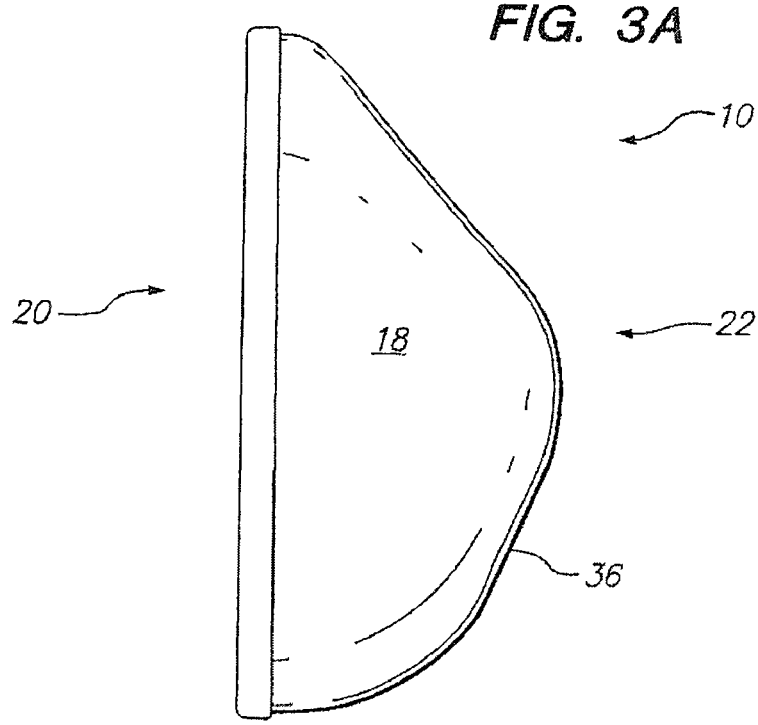
FIG. 3A is a side view of the embodiment of the inventive device of FIG. 1 which has the shape of a human breast.
Figure 3B:
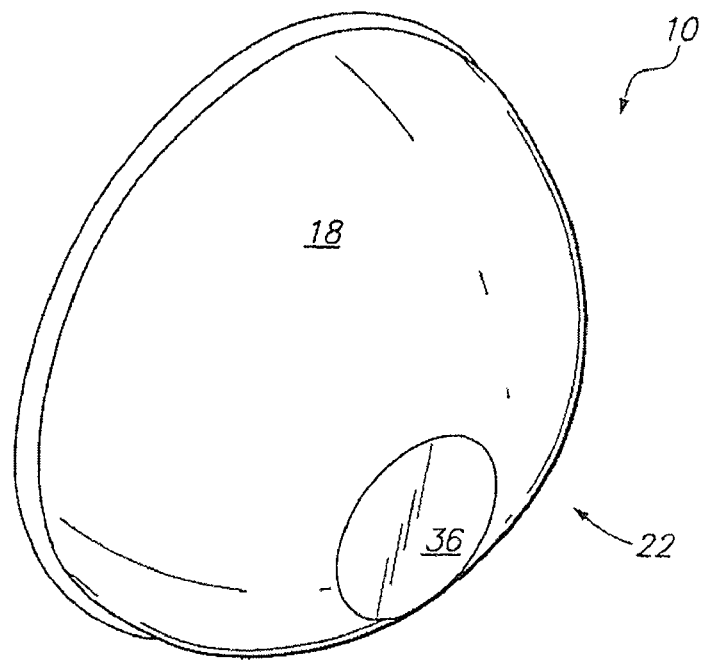
FIG. 3B is a perspective view of the embodiment of the inventive device shown in FIG. 3A.

In FIGS. 3A and 3B are shown two views of an embodiment of the device 10 which is intended to approximate the profile of a normal breast. This embodiment is shown with a flattened area 36 formed on the exterior front of the reservoir to allow the device to be set down on a flat surface, without tipping or wobbling, while containing milk. However, alternative embodiments could be made without this flattened area.

FIG. 4 illustrates the reservoir 18 being detachable from the adaptor 16. In this fashion when the interior volume 30 of the reservoir 18 is full, the adaptor 16 can be removed and the breast milk poured into a baby bottle, or other container, for storage. In this detachable embodiment, the reservoir 18 is cup-like and the adaptor 16 functions as a lid which detachably engages with the cup-like reservoir.

Figure 5B:
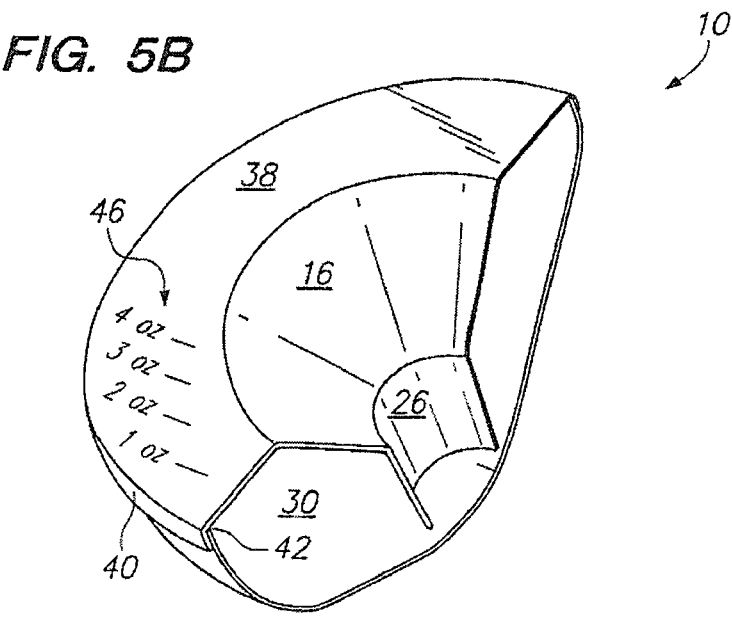
FIG. 5B is a perspective cutaway view of the inventive device of FIG. 1.
Figure 5C:
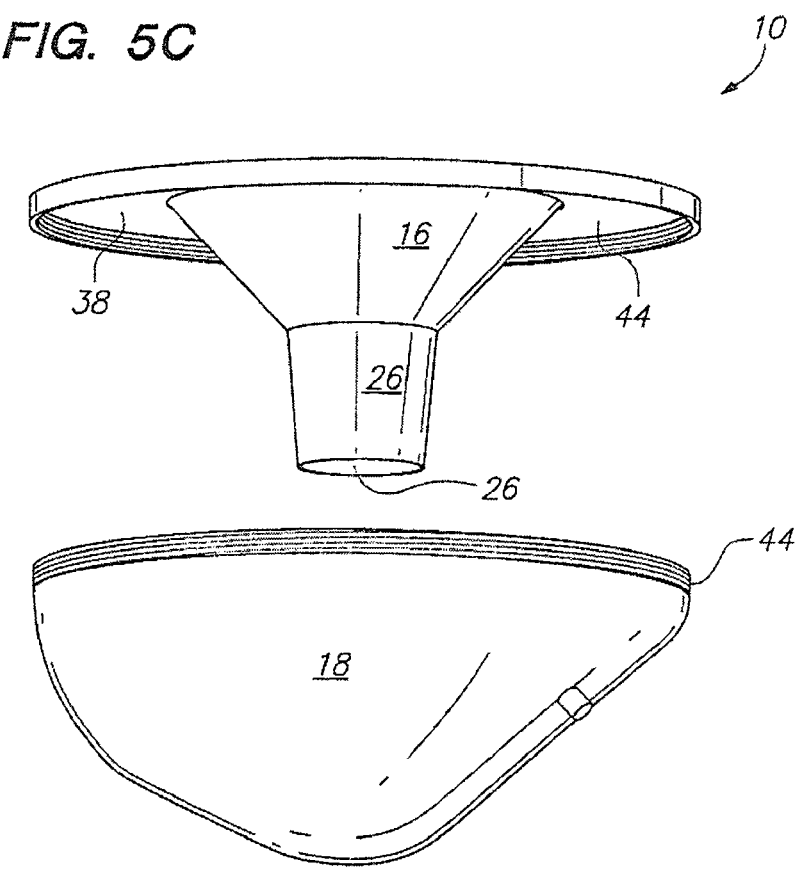
FIG. 5C is a perspective view of a screw cap embodiment of the device shown in FIGS. 5A and 5B, showing the screw cap adaptor detached from the reservoir.

Referring now to FIGS. 5A and 5B, the adaptor 16 includes a lid portion 38 which is continuous with the adaptor 16 and extends circumferentially around the cup-like reservoir 18. An overlapping lip 40 extends outward and downward from the lid portion 38 and includes a means for engaging the upper edge 42 of the reservoir 18. The engaging means can be of an overlapping snap-fit variety of a type well known in the lid fastening arts or a screw cap variety employing engaging threads 44 as shown in FIG. 5C. When attached, the adaptor 16 and reservoir 18 achieve a seal at the junction of lid portion 38 and edge 42 which cannot be compromised by the suction forces supplied by pump 12. Alternatively, the device may be one solid component, wherein the adaptor 16 does not detach from the reservoir 18 and wherein both suction and milk transfer/retrieval is accomplished through a single port hole or stem 48. Also as seen in FIG. 5B the lid portion 38 can be provided with graduations 46 denoting the number of ounces of milk contained within the reservoir 18.

FIG. 6 illustrates the inventive device 10 being used in a typical pumping cycle. A stem 48 located on the top exterior surface of reservoir 18 attaches to the pump 12 by way of a vacuum hose 50. The vacuum hose 50 attaches to the stem 48 at the top so that the pump 12 will not suction breast milk 52 into the workings of the pump 12. The pump 12 shown is a hospital grade tabletop electric pump. Additionally, although not shown, a manual pump can be employed. To further aid in the portability of the system, a belt holder 54 (See also FIGS. 1 and 2) or possibly backpack, operates to receive the electric pump 12 and allows it to be carried around while the inventive device 10 is being used. The pump 12 provides suction to the interior volume 30 of the reservoir 18 and stimulates the mother's milk to be released, or "letdown," for collection.

Examples of tabletop electric pumps presently in existence which could be used with the inventive apparatus 10 include those made by Medela, Inc., or Ameda/Hollister. These pumps can be carried in a portable manner by employing a belt holder 54 as shown in the Figures. Manual pumps which could be used include the Medela foot pump or the Versa Ped™ foot pump.

During the pumping cycle, the device 10 is located within, and supported by the brassiere (See FIGS. 1 and 2), thereby allowing the woman using the device to engage in normal workday tasks in a completely hands-free manner. A woman may use the device 10 to pump both breasts 14 at once, or else a single breast. If a woman pumps one breast 14, it is recommended that she wear the device 10 on the second breast 14 too, so that any milk 52 expressed passively, as a result of the letdown reflex, can be collected and stored.

FIG. 7 shows an alternative embodiment of the invention which is designed to further prevent leakage of expressed breast milk 52. A circular barrier 56 formed into the transition area 58 separating the narrow end of the funnel adaptor 16 and the proximal end of drip tube 24 helps prevent the backflow of expressed breast milk 52.

FIG. 8 illustrates an embodiment having the interior 60 of the funnel adaptor 16 lined with a pliable gas or liquid-filled bladder 62 for achieving enhanced sealing contact with the breast 14. The bladder 62 flexes with the shape of the breast 14 and molds the adaptor 16 thereto for enhanced sealing and comfort.

FIG. 9 shows an embodiment wherein the drip tube 24 is eliminated and, instead, the adaptor 16 narrows to an aperture 64, only, through which is placed the nipple portion 34 of the breast 14. In this version, breast milk 52 would drip directly off of the nipple 34 into the reservoir 18, without traveling down a drip tube 24. The adaptor 16 and lid portion 38 are preferably constructed from a highly flexible (possibly silicone) material which forms closely to the breast 14 to better accommodate passive breast milk collection. In addition to being used as a passive milk collector, this embodiment could also double as a false breast insert for purposes of enhancing a woman's bust line, especially if the reservoir 18 is shaped to conform to a natural breast outline.

Figure 10A:
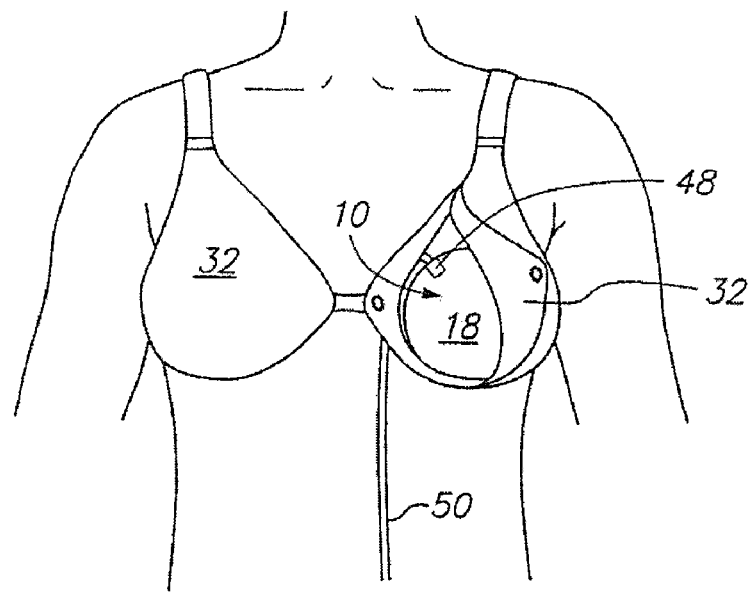
FIG. 10A is a front perspective view of a woman's torso showing the inventive device being worn in a nursing brassiere.
Figure 10B:
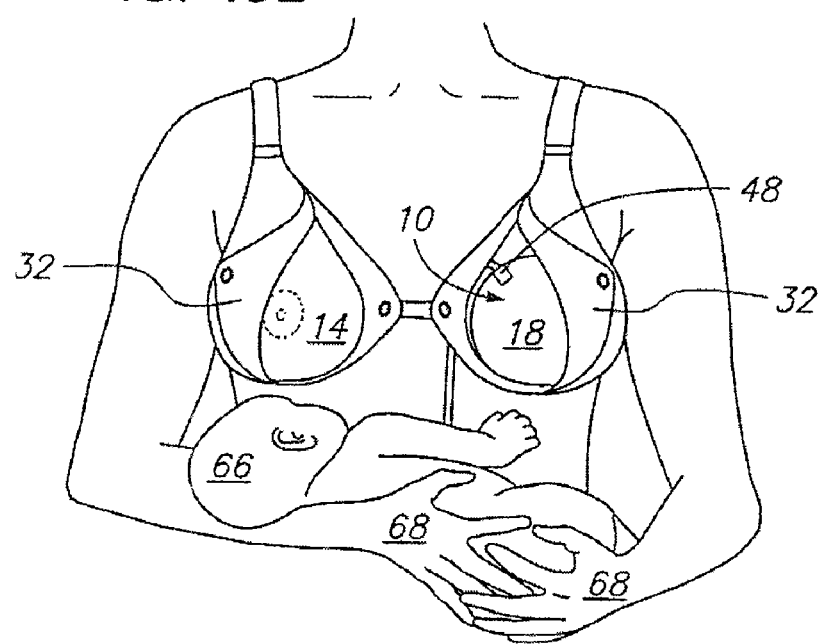
FIG. 10B is a front perspective view of a woman's torso showing the inventive device of FIG. 1 placed on the woman's left breast for milk collection while allowing her hands to remain free to nurse her infant on her opposite breast.

FIGS. 10A and 10B show the device 10 being placed within a woman's nursing brassiere 32. FIG. 10A demonstrates how such a compact device 10 may be concealed under normal clothing and used hands-free, thereby allowing a woman to carry on workplace tasks without significant interruption. FIG. 10B illustrates the hands-free advantage of the invention by showing a woman using both hands 68 to hold her nursing infant 66 on one breast 14, while either passively or actively collecting milk from the opposite breast with the device 10. Also, this illustrates how the invention can significantly simplify the nursing task for compromised infants who may nurse when the device is used with a pump on the opposite breast.

FIGS. 11A-G illustrate an alternative embodiment of the invention which introduces negative pumping pressure directly to the smaller inner sub-volume 70 of the drip tube 24 rather than to the entire reservoir volume 30 as described in the embodiments up to this point. If a similarly sized pump is used with this embodiment the negative pressure made by the same pump is enhanced in the smaller drip tube volume 70 when compared with the previous embodiments which pump the entire reservoir volume 30. This introduction of enhanced pressure may result in faster pumping of breast milk 52 particularly in women who have difficulty with initiating the letdown reflex. Furthermore, it reduces the chances of leaking from the milk reservoir.

Figure 11A:
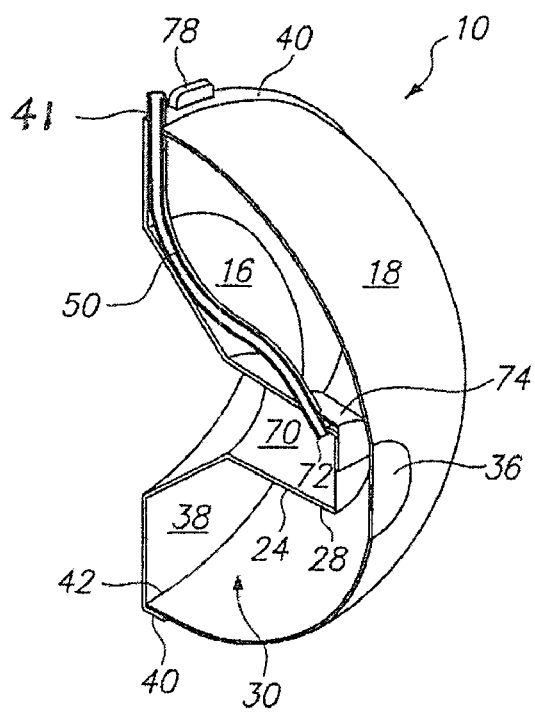
FIG. 11A is an elevated perspective cutaway view of an alternative embodiment of the inventive device which employs a valve to produce increased suction.
Figure 11B:
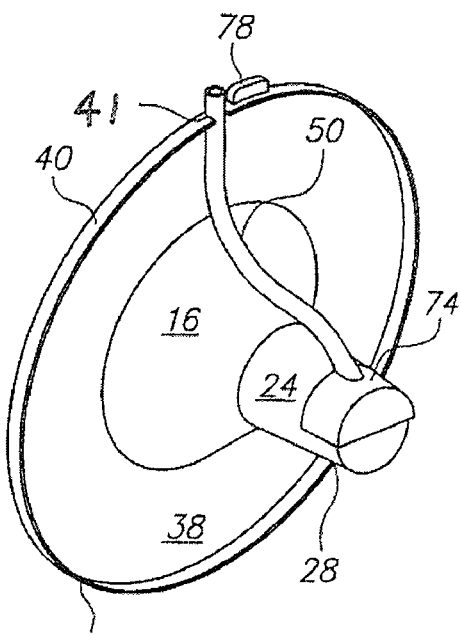
FIG. 11B is an elevated perspective view of the adaptor and valve of the embodiment of FIG. 11A shown attached to a vacuum hose.

FIG. 11A illustrates the components of the alternative embodiment 10. As shown, a vacuum hose 50 extends down through a notch 41 imparted into the lip 40 of the lid portion 38 and further extends into the drip tube volume 70 at its distal end 72. The vacuum hose 50 seats in a valve 74 which is attached to the distal end 28 of the drip tube 24. The valve 74 seals off the drip tube volume 70 when suction is applied, while alternately allowing milk to drip through into the reservoir volume 30 when suction is released. FIG. 11B shows the adaptor 16, valve 74 and vacuum hose 50 detached from the reservoir 18. The notch 41 in the lip 40 of the adaptor 16 allows the vacuum hose 50 to be snugly seated therein. A matching notch (not shown) is placed in the edge 42 of the reservoir 18 to similarly accommodate the vacuum hose 50. When the adaptor 16 is coupled to the reservoir 18, the two notches align to form a port. At the end of the pumping cycle, the vacuum hose 50 can be removed and milk 52 poured out from the reservoir 18 through the vacuum hose port.

Figure 11C:
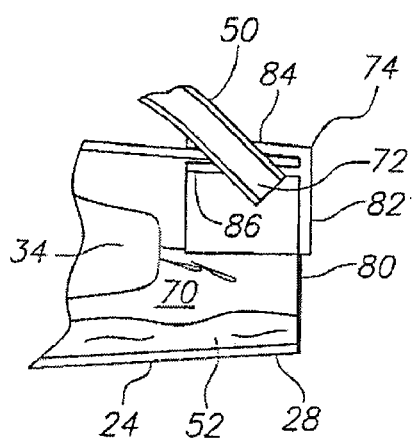
FIG. 11C is a close up side cutaway view of the drip tube, valve and distal end of the vacuum hose of the embodiment of FIG. 11A shown functioning during a negative pressure cycle.

FIG. 11C is a close up view of the drip tube 24, valve 74 and the distal end 72 of the suction hose 50 during a negative pressure cycle of the pump. With a breast 14 being inserted into the adaptor 16, the drip tube volume 70 which would be pumped would be the volume extending from the front of the nipple 34 to the distal end 28 of the drip tube 24 that is closed off by valve 74. The valve 74 is preferably a flap valve having a flap 80 which seals off the distal end 28 of the drip tube 24. A barrier 76 (See FIG. 11E), which spans across the drip tube aperture 26, prevents the flap 80 from becoming suctioned inwardly into the drip tube volume 70 during the negative pressure cycle and consequently breaking suction. However, the flap valve and aperture assembly can be modified in a number of ways so that no barrier 76 is needed. Furthermore, it is conceivable to those skilled in the art, that other types of valves such as a duckbill, or a ball valve could be used in alternative embodiments.

Figure 11D:
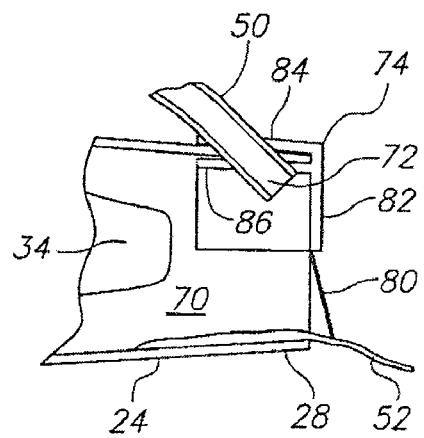
FIG. 11D is a close up side cutaway view of the drip tube, valve and distal end of the vacuum hose of the embodiment of FIG. 11A shown functioning during a positive pressure cycle.
Figure 11E:
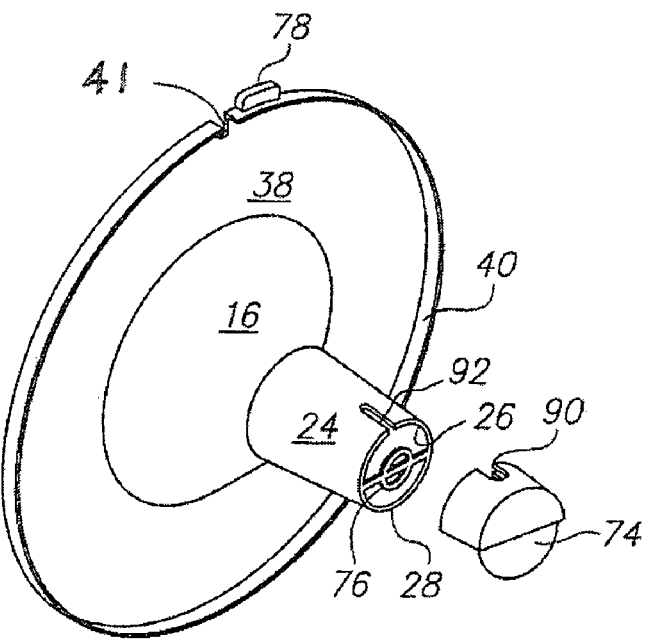
FIG. 11E is an exploded elevated perspective view of the adaptor and valve of the embodiment of FIG. 11A.
Figure 11F:
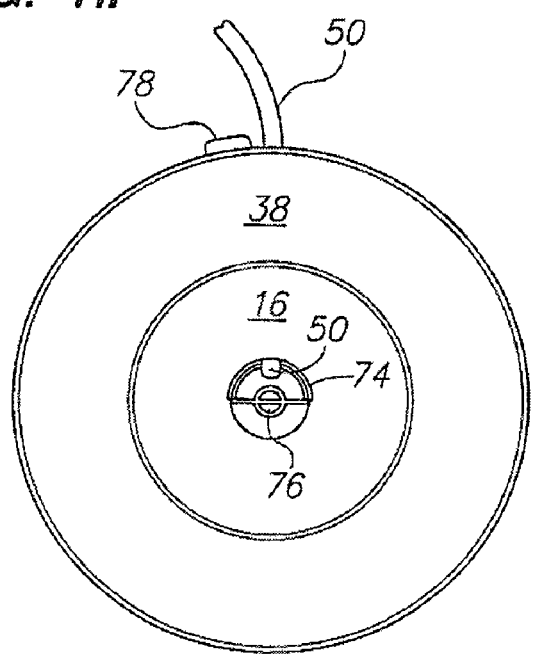
FIG. 11F is a rear view of the adaptor and valve of the embodiment of FIG. 11A.
Figure 11G:
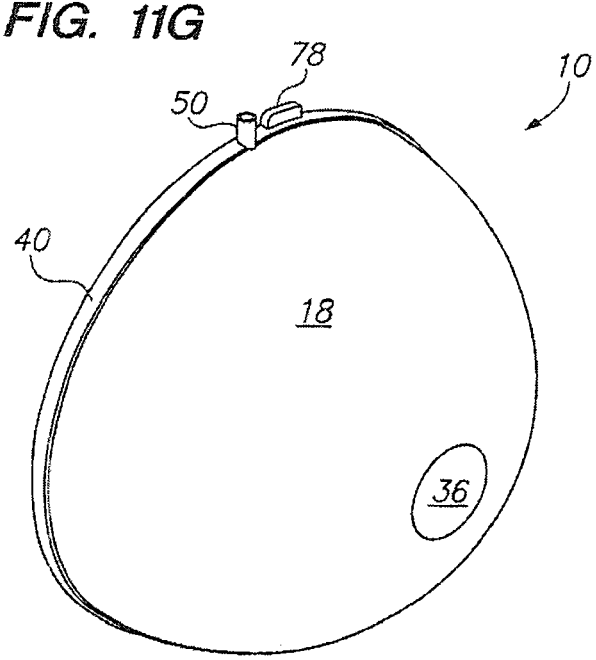
FIG. 11G is an elevated perspective view of the embodiment of FIG. 11A.

FIG. 11D shows a positive pressure cycle of the pump with the flap 80 in a relaxed state to allow the expressed milk 52 to flow into the reservoir volume 30. The barrier 76 is molded into the drip tube 24 as shown in FIG. 11E. This view illustrates the flap valve 74 disengaged from the end of the drip tube 24 to which it is attached. FIG. 11F illustrates another view of the adaptor 16 and barrier 76 showing a tab 78 molded to the lip 40 of the adaptor to allow for easy detachment of the adaptor 16 from the reservoir 18. FIG. 11G illustrates this alternative embodiment of the invention 10 fully assembled, as it might appear from the exterior.

Figure 12A:
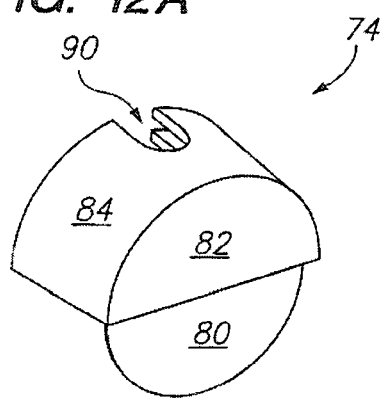
FIG. 12A is a front elevated perspective view of the flap valve component of the embodiment of FIGS. 11A-G.
Figure 12B:
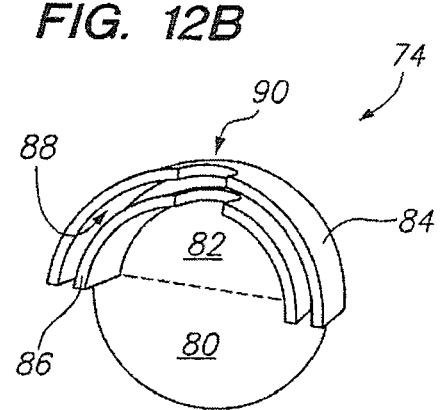
FIG. 12B is a rear perspective view of the flap valve component of the embodiment of FIGS. 11A-G.

FIGS. 12A and 12B illustrate front and rear perspective views of the preferred flap valve 74 used in the embodiment described above and shown in FIGS. 11A-G. The flap valve 74 shown is comprised of a semi-circular front face 82 from which downwardly extends the movable flap 80 shown previously in FIGS. 11C and 11D. Two stacked, semi-circular preforms 84 and 86 protrude rearward at right angles from the front face 82. The lower preform 86 has an outside circumference sized to fit snugly within the inside circumference of the drip tube 24, while the upper preform 84 has an inside circumference sized to fit snugly around the outside circumference of the drip tube 24. The space 88 located between the upper and lower preforms 84, 86 is sized to receive the distal end 28 of the drip tube 24 in the "sandwiching" manner shown in FIGS. 11C and 11D. A notch 90 is placed into each preform. The notches 90 are sized to receive the vacuum tube 50, the vacuum tube being connected to a vacuum pump as already described herein. The lower preform notch 90 is offset slightly forward of (closer to the front face 82) of upper preform notch 90, for reasons further described below. The drip tube 24 likewise has a notch 92 (See FIG. 11E) imparted inwardly from its distal end 28 for receiving the vacuum tube 50. When the flap valve 74 is installed on the distal end 28 of drip tube 24, the notches 90 of the upper and lower preforms 84, 86 of the flap valve align with the drip tube notch 92 to create a port for inserting the end of the vacuum hose 50 as shown in FIGS. 11C and 11D. As shown, the offset upper and lower notches 90 cause the vacuum hose 50 to be received into valve 74 at an angle. This angular position of the vacuum tube 50 helps prevent it from becoming disengaged from the valve 74 during pumping. The interplay of the vacuum tube 50 supplying vacuum to the inner sub-volume 70 of drip tube 24 along with flap valve 74 functioning in the manner herein described supplies an efficient and reliable mechanism for expressing milk from a woman's breast.

Figure 13A:
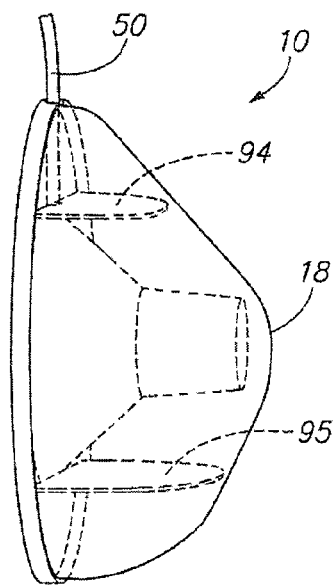
FIG. 13A is side perspective view of an alternative embodiment of the inventive device which employs baffles (shown in phantom) attached to the interior volume of the reservoir to reduce pumping volume.
Figure 13B:
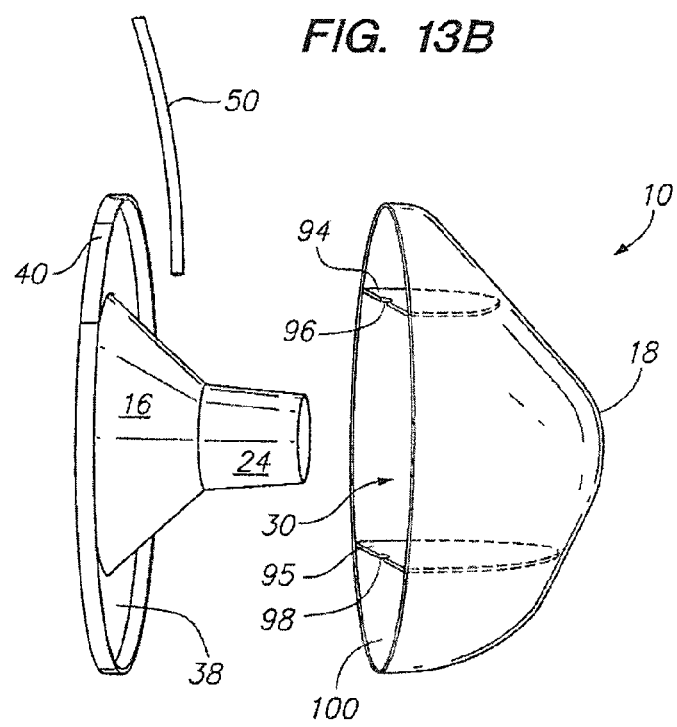
FIG. 13B is an exploded side perspective view of the embodiment shown in FIG. 13A.

FIG. 13A illustrates yet another alternative embodiment of the invention 10. This embodiment increases pumping efficiency by introducing baffles 94, 95 into the interior volume 30 of the reservoir 18. Baffles 94, 95 are attached to the interior sides of reservoir 18 and seal off a sub volume 30 between the baffles. Upper and lower baffles 94, 95 are spaced to accommodate the funnel portion of adaptor 16, there between, when the adaptor 16 is coupled to the reservoir 18 as shown in FIG. 13A. Vacuum hose 50 is introduced to the sub-volume 30 between baffles 94, 95 via notch 96 located in the upper baffle 94. The lip 40 and reservoir 18 have mating cutouts as described previously which form a port to allow entry of vacuum hose 50. The lower baffle 95 has a valve 98 (check # on drawing) to allow milk to drip into the lower portion 100 of the reservoir 18. When suction is introduced, the baffles 94, 95 reduce the interior volume 30 required to be pumped within the reservoir and a high negative pressure zone is created. If the same pump is used, the amount of suction is greater with baffles 94, 95, compared to when baffles are eliminated from the reservoir 18 (in which case the pump would be working against the entire reservoir volume 30). The advantage of this design is that fewer parts are required for assembly and cleaning.

Figure 14:
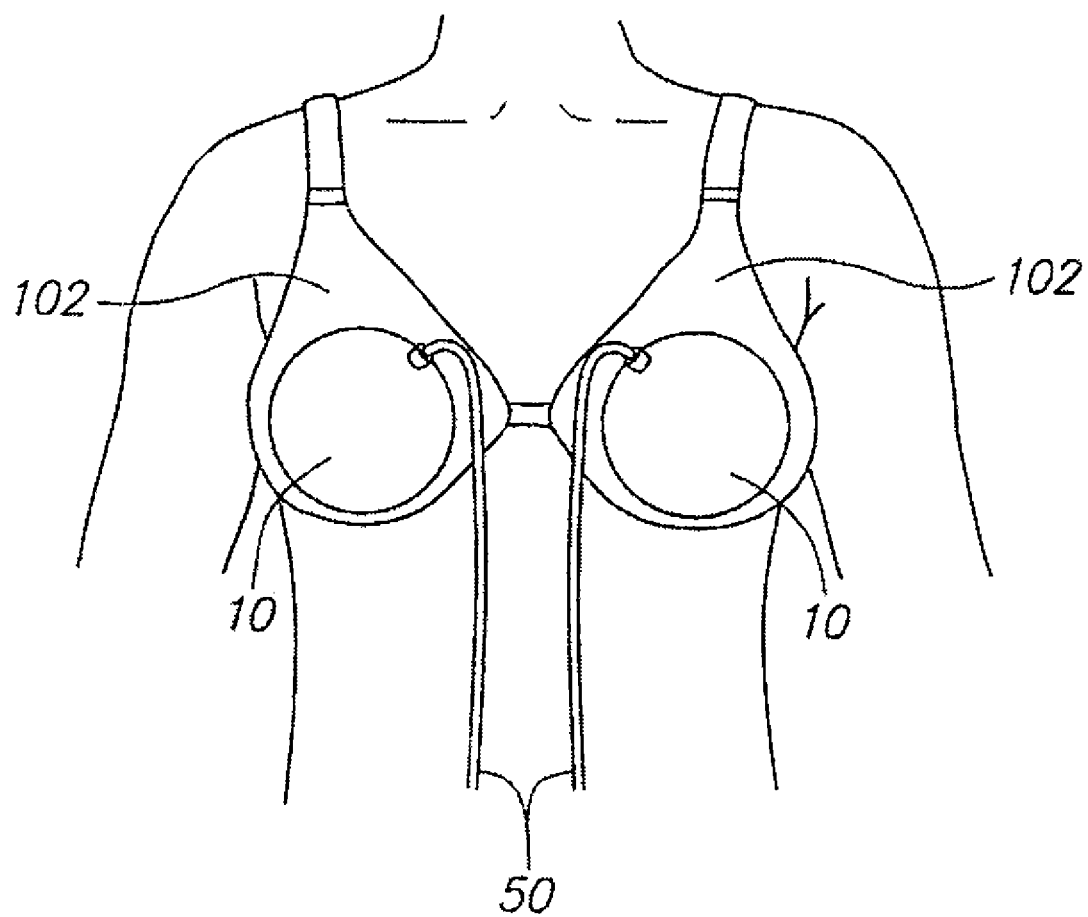
FIG. 14 is a perspective view of an alternative embodiment of the inventive device which is coupled to a suspension system, this embodiment not being dependent upon a brassiere for support upon a woman's breasts.

FIG. 14 illustrates yet another embodiment of the invention 10 which employs a system of brassiere-like adjustable straps 102 coupled to the invention 10. This allows the device to be worn like a brassiere by the wearer.

FIGS. 15-27 illustrate additional embodiments of the breast milk collection device 200 which includes a valve assembly and baffle structure configured to prevent overflow of milk into the pump and associated vacuum line. The tapered fits and smooth surfaces of the various parts of this embodiment allow the device to reliably seal on multiple surfaces and allow use of a vacuum pump without expressed milk backing up into the vacuum pump and hose system, as will be described below. The structural features and function of the illustrated embodiments also help reduce build up and bacterial growth in the collection device, thereby reducing contamination risk in the expressed breast milk. In addition, the individual parts comprising the valve assembly of these embodiments can be readily disassembled for cleaning, and due to the unique use of keyways, keys, slots and mating angled portions, the individual parts can be re-assembled in only one, correct way by the user after cleaning.

Referring to FIG. 15-17, the illustrated embodiment of the inventive device 200 includes an adaptor 216 within which a woman's breast is inserted. The adaptor 216 opens into a reservoir 218 that collects and stores breast milk being expressed from the breast. In the illustrated embodiment, the adaptor 216 is cone or funnel shaped to form a seal with the breast during the milk expression process. As shown in FIGS. 15-17, the funnel-shaped adaptor 216 has a first end 217 which opens to the rear 201 of the collection device 200, and a second end 219 forming a drip tube that, in the assembled device, is adjacent the front end 222 of the device 200. As described for previous embodiments, the adaptor 216 protrudes a distance into the confines of the reservoir's interior volume 230 to provide the device 200 with a compact configuration. The adaptor 216 may be formed from a variety of materials including polypropylene, silicone, or other materials which may be capable of forming a superior seal around the breast or making the adaptor 216 more comfortable for a user.

The illustrated embodiment shows a flattened area 236 formed on the front end 222 of the reservoir 218, which allows the device to be set down on a flat surface without tipping or wobbling and prevents spillage when the device 200 contains milk. The general structure and function of the breast adaptor 216 and the reservoir 218 is otherwise similar to that described for the previous embodiments. As previously discussed, various electromechanical or manual pumps known in the art may be used with the illustrated embodiment to provide alternating vacuum pressure to the user's breast.

Figure 19:
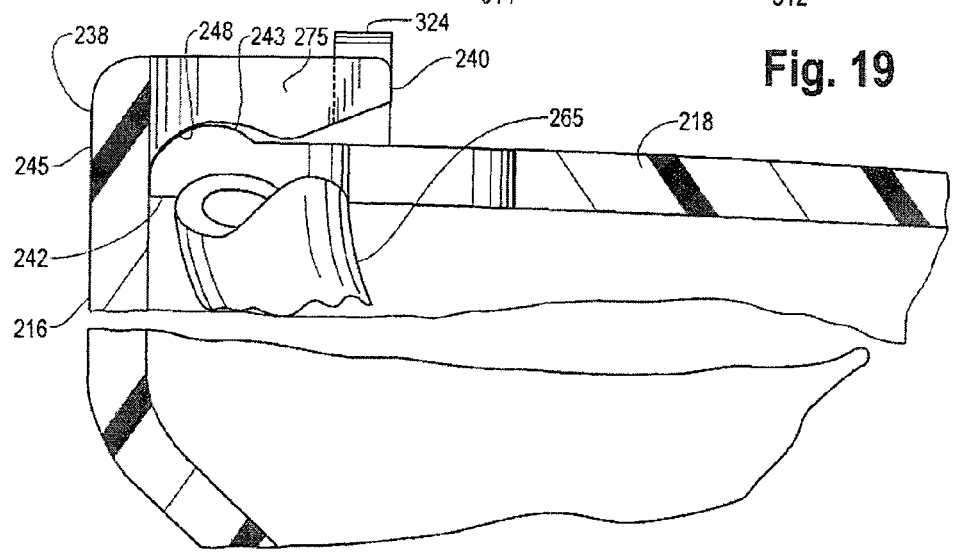
FIG. 19 is a detail sectional view of the connection between the breast adaptor and the reservoir of the embodiment shown in FIG. 15.

FIGS. 16 and 19 illustrate an embodiment of the device where the adaptor 216 is readily manually detachable from the reservoir 218. As described for the previous embodiments, when the interior volume 230 of reservoir 218 is full, the adaptor 216 can be removed from reservoir 218 and the breast milk emptied into a baby bottle or other container for storage. Further, the adaptor 216 must be removed from reservoir 218 to access the interior parts of the collection device 200, as will be explained. Referring to FIG. 19, the adaptor 216 further includes a lid portion 238 which is continuous with the adaptor 216 and extends circumferentially around the reservoir 218. An overlapping flange 240 extends outward from the lid portion 238 and engages the upper lip 242 of the reservoir 218. In the illustrated embodiment of FIG. 19, a molded snap bump 243 integrally formed in the reservoir 218 engages a corresponding cradle 248 in the adaptor 216 to maintain the adaptor 216 in a fitted and sealed position connected to the reservoir 218. Other overlapping fasteners known in the art may also be employed as described for previous embodiments. Due to the inherent flexibility of the materials from which adaptor 216 is constructed, flange 240 flexes outward when adaptor 216 is manually removed from, or assembled with reservoir 218 as cradle 248 slides over snap bump 243.

Referring to FIGS. 16-18 and 20-21B, a three-part valve assembly 250 is removably mounted concentrically on the drip tube at the second end 219 of the breast adaptor 216. The valve assembly 250 comprises a valve body 252, a valve cap 254 mounted concentrically on the valve body 252, and a valve flap 256 flexibly attached to the valve cap 254. The valve assembly 250 in its operative position is mounted over the second end 219 of the breast adaptor 216, and alternately opens and closes communication between the breast adaptor 216 and the reservoir 218 as the vacuum pump (not shown) alternates between a negative or vacuum pressure and approaches a neutral or positive pressure, as will be explained. In the illustrated embodiment shown in FIGS. 16, 20 and 21, the second end 219 of the breast adaptor 216 has an enlarged opening 251 on the top side to allow the flow of positive, neutral or negative air pressure from the vacuum line 265 leading to the vacuum pump, and through an overflow chamber 258 formed by the valve assembly 250. A baffle structure 260 is attached to the valve cap 254 to provide a torturous path for the air pressure to flow between vacuum hose 265 and the user's breast, and to assist in substantially preventing an overflow of milk from entering the vacuum line 265 or pump assembly, as will be explained.

Figure 18:
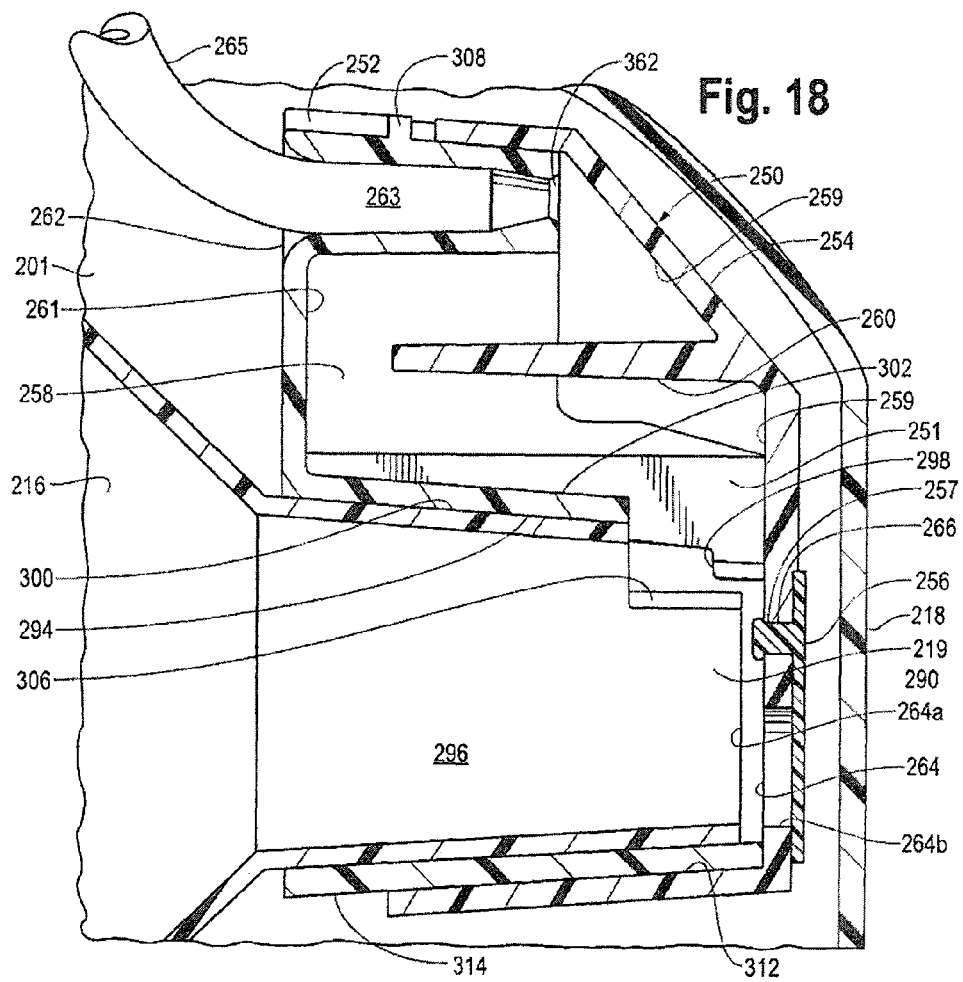
FIG. 18 is a detail cross-sectional view of the breast adaptor, valve assembly, and reservoir of the embodiment of the present invention shown in FIGS. 15 and 16.

As seen in FIGS. 16-18, the valve body 252 further includes a port 262 communicating with a channel 263 for a direct and removable connection of an external suction source to the valve assembly 250. Suction or vacuum hose 265 in this embodiment is removably inserted directly into inlet port 262 at the rear top of the valve body 252. The opposite end (not shown) of vacuum line 265 is connected to a vacuum pump of the type known to those skilled in the art to alternately apply positive, ornamental and negative pressure to the user's breast to facilitate the expression of milk. In the illustrated embodiment of FIGS. 16-18, the inlet port 262 is adapted to receive suction or vacuum hose 265 by providing a tapered female fitting formed integrally by channel 263 in the valve body 252. The valve assembly 250 creates an indirect path between adaptor 216 and vacuum line 265 to prevent expressed milk under heavy flow conditions from flowing back through the suction path to vacuum hose 265 and to an external pump (not shown) as will be explained.

The valve cap 254 as seen in FIGS. 16 and 18 is slidably and sealingly positioned concentrically over the valve body 252 and further includes baffle structure 260 integrally formed with an interior wall 259 of the valve cap 254. Baffle 260 extends substantially perpendicular to the lower portion of interior wall 259. When the valve cap 254 is in the assembled concentric position around the valve body 252 (FIG. 18), the baffle structure 260 extends axially into the central portion of overflow chamber 258, and terminates prior to reaching end wall 261 or either side wall of overflow chamber 258, thus creating a space between baffle structure 260 and side walls and end wall 261 of the overflow chamber that provides a torturous and diffuse path through chamber 258 for the flow of positive and negative air pressure from vacuum line 265 to breast adaptor 216. The baffle structure 260 also combines with overflow chamber 258 to prevent the back flow of milk through valve body 252 and to the vacuum line 265 and associated pump.

Figure 21:
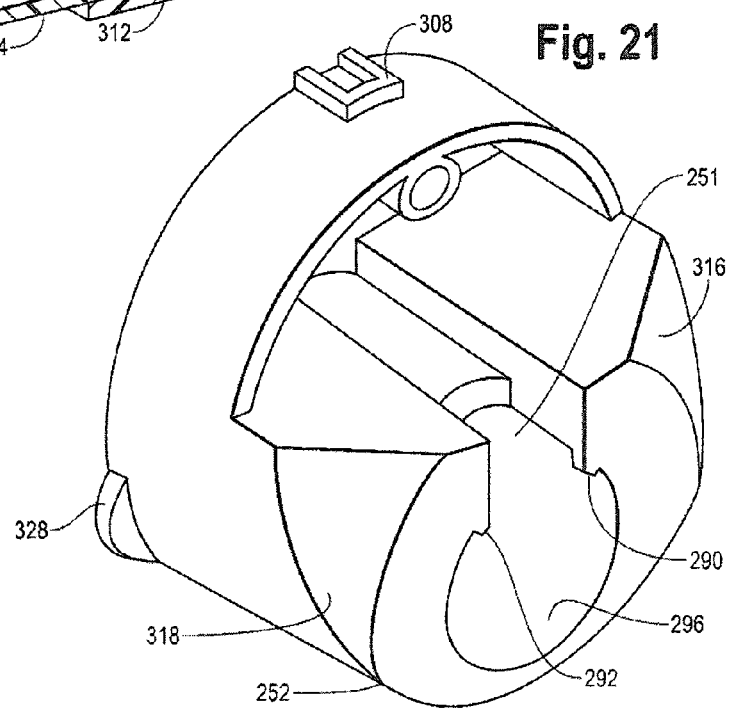
FIG. 21 is a front perspective detail view of the valve body of the valve assembly for the embodiment shown in FIG. 15.
Figure 21A:
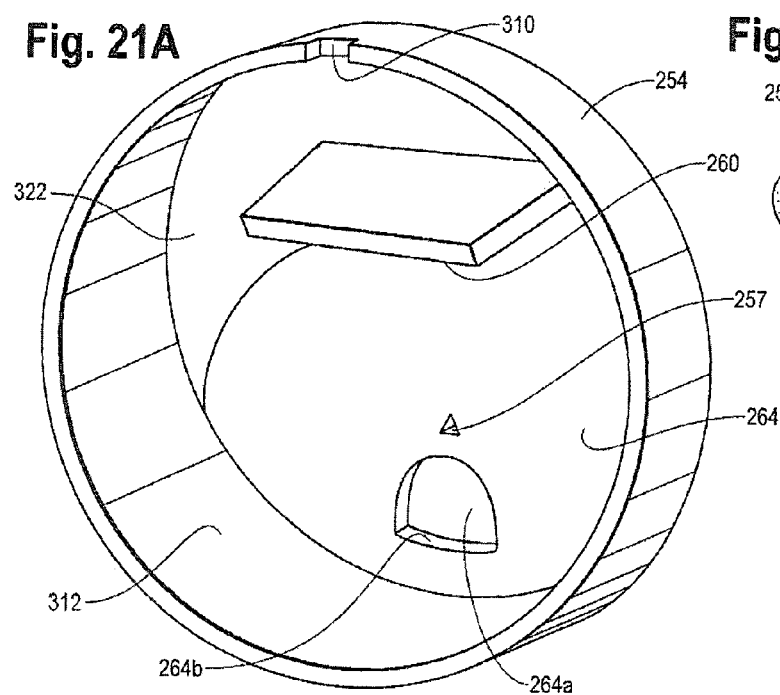
FIG. 21A is a rear perspective view of the valve cap and baffle of the embodiment shown in FIG. 15.
Figure 21B:
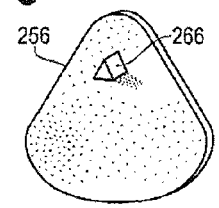
FIG. 21B is a detail perspective view of the valve flap of the apparatus shown in FIG. 15.

In the assembled concentric position shown in FIGS. 15, 16 and 18, flap valve 256 releasably closes off aperture 264b formed in valve cap 254. Aperture 264b is in communication with larger aperture 264a in valve body 252, and with aperture 264 at second end 219 of adaptor 216. The flap valve 256 may be molded from a soft, flexible rubber-like plastic or other material and includes a flexible pin 266 extending perpendicular to the surface of the flap valve 256. The pin 266 is press fit into an aperture 257 in the valve cap 254 to hold the flap valve 256 in place flush against aperture 264b of the valve cap 254 to cover the aperture 264, 264a and 264b during the negative or vacuum pressure portion of the pumping cycle. Flexible pin 266 has a predetermined polygoval cross sectional shape, such as triangular as shown in FIG. 21B. Valve cap 254 includes corresponding aperture 257 having the same polygoval peripheral shape as pin 266, with aperture 257 located above aperture 264b (FIG. 21A). Upon assembly of flap valve 256 is flush against the portion of valve cap 254 surrounding aperture 264a. Pin 266 may also include a slightly longer protruding portion (not shown) extending in the radial direction on pin 266 at a distance substantially equal to the thickness of valve cap 254. This protruding portion will prevent pin 266 from sliding out of aperture 257 during heavy milk flows, or during the application of positive pressure through valve assembly 250. The polygoval shape of aperture 257 and pin 266 enable the flap valve 256 to be correctly assembled in only one way by the user. With the flap valve covering aperture 264a, the flap valve 256 cannot be moved angularly away with respect to aperture 264a, since the polygoval, or triangular, shape of pin 266 and aperture 257 prevent the flap valve from being incorrectly connected to valve cap 254, or rotated to an incorrect position once properly installed.

The valve flap 256 thus encloses the space within the drip tube at the second end 219 of the breast adaptor 216, overflow chamber 258 of valve assembly 250, and suction line 265 during a negative pressure cycle of the pump. Conversely, the valve flap 256 opens during the positive pressure cycle of the pump allowing the expressed milk to flow through apertures 264, 264a and 264b and into the collection volume 230 of reservoir 218. When the flap valve 256 closes off the apertures 264, 264a and 264b, a reduced volume is created within the second end 219 of the breast adaptor 216 compared with the size of reservoir collection volume 230. When suction is introduced to this reduced volume, the reduced volume becomes an efficient negative pressure zone, drawing the breast and nipple forward, sealing the breasts to adaptor 216, and encouraging the expression of breast milk from a woman's breast.

In the illustrated embodiment of FIG. 21B, the flap valve 256 is generally triangular in shape with rounded corners. One advantage of this shape is to alert the user if the flap valve 256 is not oriented properly during reassembly after cleaning. Also, the aperture 264b that flap valve 256 covers is as large as possible to allow the escape of milk to reservoir 218 when large amounts of milk are expressed in a short period of time. The size of aperture 264b compliments the overflow chamber 258, so that milk that backs up into the overflow chamber during the negative or suction portion of the pump cycle escapes through aperture 264b as soon as negative pressure is released and flap valve 256 opens aperture 264b. In the illustrated embodiment, flap valve 256 is made of advanced polymer materials that provide flexibility and memory to the flap valve, while also achieving the necessary surface tension between the flap valve and valve cap to hold a suction inside valve assembly 250 and adapter 216. The curved edges of the triangular configuration of the illustrated flap valve 256 keep the flap valve from bending and creasing during suction, thereby maintaining the integrity of the vacuum The overflow chamber 258 and baffle structure 260 combine to create an overflow capacity for the second end 219 of the breast adaptor 216 that prevents breast milk from entering and contaminating the vacuum line 265 and the associated vacuum pump mechanism during a suction portion of the pumping cycle. The various elements comprising breast milk collection device 200 described above are adapted to be easily drained and cleaned after each use, eliminating the possibility that milk can remain on the various parts long enough to spawn the growth of bacteria. Likewise, the configuration of valve body 252 with overflow chamber 258, and of valve cap 254 with baffle 260 extending into overflow chamber 258, specifically prevents breast milk from entering vacuum line 265 and the associated vacuum pump which may not be as easy to clean as are adaptor 216, valve body 252, valve cap 254 and flap valve 256. The space created between overflow chamber 258 and the baffle structure 260, and the second end 219 of the breast adaptor 216, including opening 251 leading from second end 219 and overflow chamber 258, allows the breast milk collection device 200 to deal effectively with sudden, intermittent large letdowns of milk. The baffle structure 260 and overflow chamber 258 may be employed infrequently during operation, as the majority of the expressed milk may trickle out of the nipple in small quantities and proceed directly through apertures 264, 264a and 264b and through flap valve 256 into the interior volume 230 of reservoir 218. As described above, in certain circumstances when the letdown of milk in a single cycle is large enough that milk reaches the flap valve 256 before the suction of the pump's negative pressure cycle is released, expressed milk can back up into the overflow chamber 258 under the force of the vacuum pressure. The pump pressure cycling between negative and positive pressures in the enclosed area formed by the closing of flap valve 256 can create significant turbulence in a volume of milk which is trapped in the second end 219 of the breast adaptor 216 before traveling through the valve flap 256 and into the reservoir 218. The milk may bubble, and become airborne due to the suction force. If milk is flowing from the nipple, aerating inside the adaptor 216, and attempting to follow the suction path, the baffle structure 260 will diffuse the aerated milk by interrupting its path toward the vacuum line 265. Milk sprayed up into the overflow chamber 258 will be deflected or redirected off of the baffle structure 260 and toward the interior surfaces of the valve assembly 250 and of overflow chamber 258. The surrounding walls of the overflow chamber 258 in the valve assembly 250 are configured to allow milk to drain back down into the adaptor 216 and through the flap valve 256 into the reservoir 218 during portions of the pumping cycle when the negative pressure is released.

Figure 22:
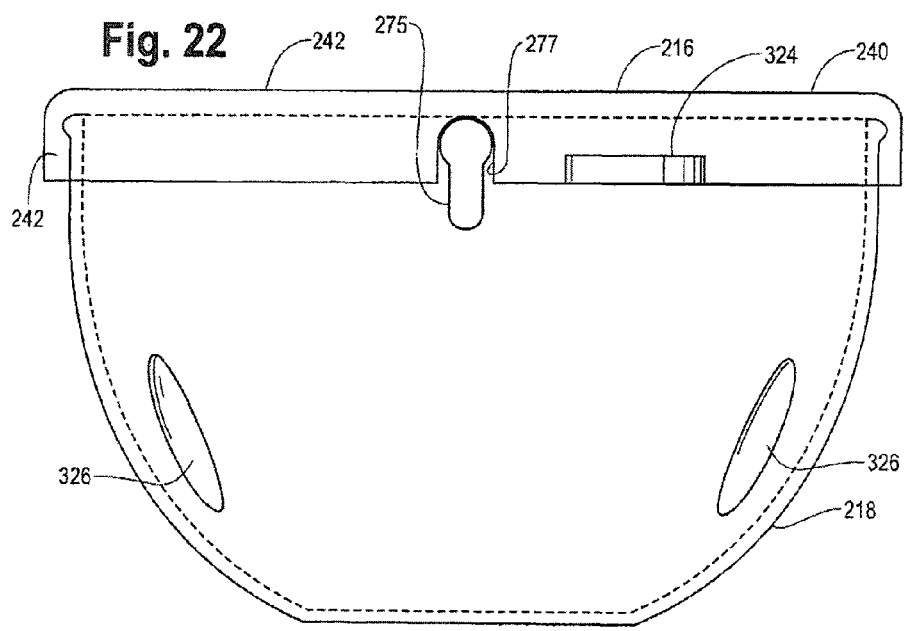
FIG. 22 is a side view of the embodiment of the present invention shown in FIG. 15, illustrating the combined vacuum tube access slot and pour spout on each of the reservoir and the adaptor.

Referring to FIG. 22, a slot 275 is integrally formed in the upper lip 242 of the reservoir 218. The slot 275 is also aligned with a corresponding notch 277 integrally formed in the flange or lip 240 of the adaptor 216. The vacuum hose 265, which is ultimately connected to a vacuum hose 272 (FIG. 23) extending from the external suction source extends down through slot 275 (FIGS. 19, 22) where the hose 265 connects to channel 263 of the valve assembly 250 (FIG. 16). The slot 275 also provides a vent to accommodate the necessary fluctuations of air volume in the reservoir 218 due to alternating positive and negative pressures created as a result of the pump cycling, and due to the changing volume of milk in reservoir 218. The shape of the slot 275 further provides a pour spout allowing the user to easily and simply pull the vacuum hose directly out of the channel 263 of the valve body through the slot 275, and transfer milk to a baby bottle or other storage device without having to remove the lid adaptor 216 from the reservoir 218 and risk spillage. When the device 200 is inverted to pour the milk into another container, the flap valve 256 moves to its open position, and acts as a pressure relief mechanism for the reservoir's interior volume, allowing air to mix with the exiting milk stream, with air replacing the milk in the reservoir's interior volume, resulting in a smooth steady flow of milk without air bubbles or "gurgling," while pouring. This is important since most storage devices are baby bottles with relatively small diameter openings to pour into.

Figure 23:
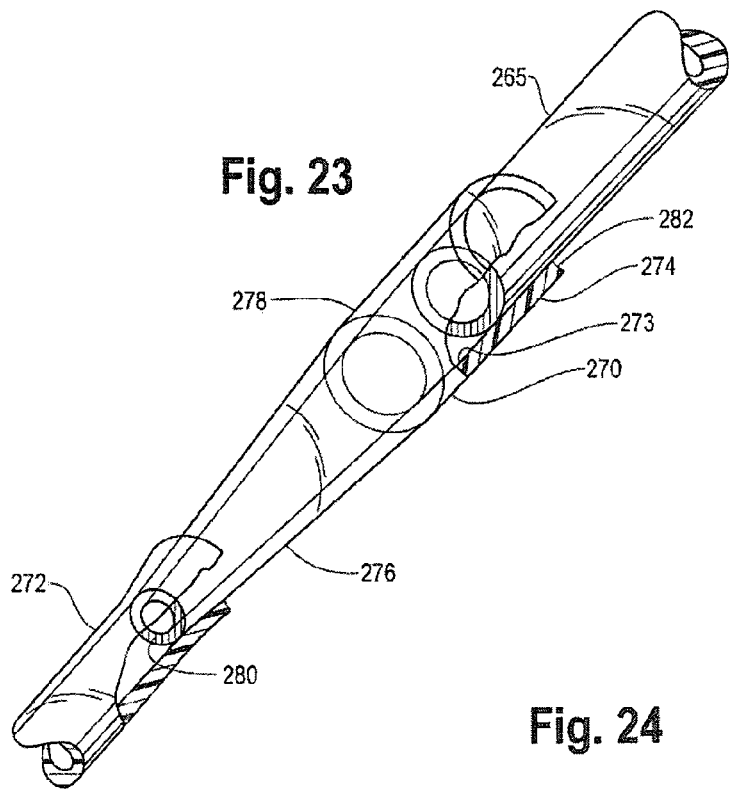
FIG. 23 is a front perspective partially cut-away assembly view of the tubing fitting for the vacuum hose connection apparatus for the embodiment shown in FIG. 15.

Referring to FIG. 23, the collection device 200 may further include a detachable external connection apparatus 270 which connects the vacuum line 265 that is attached to the collection device 200 to a vacuum line 272 extending from the external suction source or pump (not shown). The connection apparatus 270 provides a user with flexibility and convenience during the process of pumping breast milk. In the illustrated embodiment, the connection apparatus 270 is a partially tapered tubular fitting having outer male and female ends, and a hollow channel 273 extending the length of the connector apparatus. Connection apparatus 270 includes a first portion 274 having an outer diameter that may be cylindrical or slightly tapered. A second portion 276 of connection apparatus 270 is tapered from end 278 of first portion 274 to the male end 280 of second portion 276. The end 282 of first portion 274 provides the female end of the connection apparatus 270, as will be explained. The interior and exterior dimensions of connection apparatus 270 are calculated to accommodate various sizes of vacuum hoses 272 for a wide variety of pumps on the market. Other embodiments may also include tubular fittings having male/male connections or female/female connections. One of ordinary skill in the art will appreciate that the connection apparatus 270 should create a sufficient seal between the vacuum hoses 265, 272 to operate the device 200 at the appropriate vacuum pressure while facilitating the easy, frequent and reliable assembly and disassembly of the vacuum pump connection, so as to facilitate optimal user flexibility before, during and after pumping has been initiated, interrupted, resumed and completed.

In the illustrated embodiment of FIG. 23, the tapered second portion 276 of connection apparatus 270 allows easy insertion of hose 272 over end 280 to create the necessary seal and to also provide for easy assembly and disassembly. Also, channel 273 at end 282 of connection device 270 is dimensioned to receive vacuum line 265 and to accommodate some variations in the outer diameter, and to tightly fit around the outer diameter of vacuum line 265, by means of a slightly tapering internal channel, thus forming a seal between the vacuum line and the connector apparatus. The external connection apparatus 270 allows a mobile user to assemble the device under her clothing and into a brassiere privately, and then move to another location, if necessary, to connect the collection device 200 to a pump which may be left in a stationary location such as a workstation via the connection apparatus 270. In this scenario, the vacuum line 265 could protrude slightly from under a user's clothing, or be hidden, and remain easily accessible to provide a simple and secure connection to an external pump. With the external connection apparatus 270, a user may easily interrupt the milk pumping process to tend to ongoing or unexpected tasks at work or at home without disassembling all the equipment, undressing, and/or cleaning up leaking milk. A user may also continue pumping breast milk discreetly into one or two collection devices 200 located in the user's bra in the presence of others without the need to relocate to another area because of the need for social modesty, or to partially undress, as required by most other hands free systems. When pumping is complete, a user may then proceed to a private place, remove the collection devices 200, transfer the milk to storage containers, and clean the devices prior to the next pumping session. Or, because of the device's innate hands free, ergonomic, secure and concealed nature, the user may engage in some other more pressing tasks not related to the task of pumping and engage those tasks after disconnecting from the pump, but in advance of finishing up the pumping process, and then later remove the devices, transfer milk and clean and prepare for the pumping next session.

The human breast milk collection device 200 of the present invention includes features that render the device easy to disassemble, clean and re-assemble by the nursing user. Each of the parts comprising the collection device 200 are specifically configured to fit together when assembled through tapered surfaces to form the seals necessary to prevent the milk from leaking from the device 200, or as explained previously, from entering the vacuum line 265, 272 or the mechanical parts of the vacuum pump (not shown). The several parts of the collection device are also configured for ready disassembly for cleaning and decontamination, such as in a normal household dishwasher, sterile cleanser hand cleaning or the like by the user after the milk expression and collection process has been completed and the reservoir 218 has been emptied of milk. In addition, as explained below in greater detail, the components of the breast milk collection device 200 can only be reassembled in their correct orientation by the user after cleaning.

Figure 20:
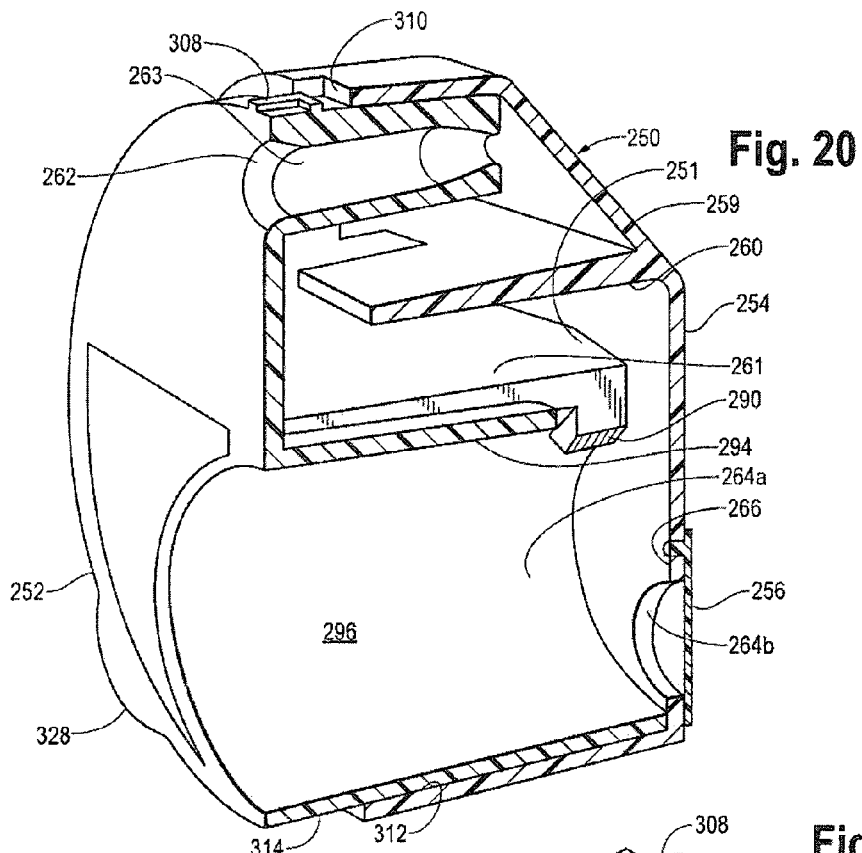
FIG. 20 is a cross-sectional perspective view of the valve assembly for the embodiment of FIGS. 15 to 18.

The second end or drip tube 219 of the adaptor 216 comprises a circular and smooth outer surface 300 that tapers in the axial direction towards second end 219, as seen in FIGS. 16-18. A corresponding circular and smooth inner surface 294, that tapers in the same axial direction as outer surface 300, is formed on the wall portion 302 of valve body 252 that forms passageway 296 (FIG. 20.).

Referring to FIGS. 16-18 and 21, a pair of projections 290, 292, extend downward and inward from the interior tapered circular surface 294 forming passageway 296 of the valve body 252. When the second end 219 of adapter 216 is inserted into chamber 296 in an improper circular orientation, the edge or end 219 of valve body 252 will abut the ends 298 of projections 290, 292, preventing tapered surface 294 of valve body 252 from properly seating on, and forming a seal with, corresponding tapered outer surface 300 of adaptor 216 (FIG. 18). Upon rotating valve body 252 into its proper orientation with respect to second end 219 of adaptor 216, the sidewalls 306 (FIG. 18) of large opening 251 will slide to a position adjacent to, and not abutting, projections 290, 292, as best seen in FIG. 18. In this orientation, tapered circular surface 294 of valve body 252 tightly engages tapered circular surface 300 of adapter 216, thus forming a seal between valve body 252 and second end 219 of adaptor 216. In use, after the user has washed the disassembled adaptor 216 and valve body 252 (FIG. 17) the valve body 252 is rotated while being slid over surface 300 of the second end 219 of adaptor 216. Not until sidewalls 306 (FIG. 18) of opening 251 in valve body 252 are in proper alignment with projections 290, 292, as explained above, will the user be able to make the proper tight sealing fit between surface 300 of the adaptor 216 and surface 294 of the valve body 252.

In similar manner, the re-assembly of valve cap 254 over the valve body 252 can only be accomplished when the valve cap and the valve body are properly concentrically rotatably oriented. To this end and referring to FIGS. 16-18, 21 and 21A, a key 308 is mounted on the upper surface of valve body 252. A corresponding keyway slot 310 is located on an upper portion of valve cap 254. When the user assembles valve cap 254 and the valve body 252 by inserting valve cap inner surface 312 over valve body outer surface 314 with baffle 260 inserted into overflow chamber 258, the valve cap 254 is rotated so that keyway slot 310 is aligned with key 308. The valve cap and valve body are then moved together, as shown in FIGS. 18 and 20, until a seal is formed between valve cap inner surface 312 and valve body outer surface 314, and key 308 is lodged in keyway slot 310, ensuring the proper rotational orientation between valve body 252 and valve cap 254, and the proper location of baffle 260 in overflow chamber 258.

A second structural relationship between valve body 252 and valve cap 254 ensures that the valve body and valve cap are properly oriented when re-assembled after cleaning. Referring to FIG. 21, valve body 252 includes a pair of contoured outer surfaces 316, 318 that are slightly curved over their respective extents. Valve cap 254 includes a contoured inner surface 320 having a pair of downward extending curved portions 322 (FIG. 21A). Contoured surfaces 316, 318 of valve body 252 are adapted to contact or closely abut contoured portions 322 of valve cap 254 in a mating relationship when valve cap 254 is slid over valve body 252 during re-assembly. If the valve body 252 and valve cap 254 are not properly circumferentially oriented, the contoured surfaces 316, 318 and 322 will not coincide, and the valve body 252 and valve cap 254 cannot be forced into a misaligned fitting juxtaposition.

The assembly and disassembly of adaptor 216 and reservoir 218 in the illustrated embodiment is also facilitated by the use of finger tabs that are adapted to be gripped by the user. As seen in FIGS. 19 and 22, a finger tab 324 is disposed on the outer surface of flange 240 of the adaptor 216. Also, referring to FIG. 22 a pair of finger indentations 326 are located on the outer surface of reservoir 218. When the user desires to separate adaptor 216 from reservoir 218, two fingers of one hand are each placed in indentations 326 and a slight gripping pressure is applied to reservoir 218. A finger or thumb of the other hand is placed on finger tab 324, and upon moving the hands apart, the adaptor 216 is separated from reservoir 218 as snap bump 243 emerges from cradle 248 (FIG. 19).

In like manner, a pair of finger tabs 328 (FIGS. 20, 21) are located on opposite sides of the outer circumference of valve body 252. The finger tabs 328 extend radially outward and are adapted to be grasped by the user's fingers when disassembling valve body 252 from adaptor 216 by sliding valve body 252 in an axial direction away from second end 219 of adaptor 216. In similar fashion, finger tabs 328 are grasped by the user when separating valve cap 254 from valve body 252.

In the illustrated embodiment, finger tab 324 is located on the adaptor 216, and finger tabs 328 are disposed on the valve body 252. It is within the scope of the present invention to include finger tabs on the valve cap 254 and reservoir 218 if desired to assist the user in the assembly and disassembly of the breast milk collection device 200 of the present invention.

In an embodiment of the present invention, at least a portion of the components required in assembling the device 200 may be manufactured from an antibacterial material to reduce the chance of bacterial growth and reduce risk of contamination in the expressed breast milk. The antibacterial material can be in the form of a special coating, or parts may be fabricated from a material which integrally possesses antibacterial properties. One of ordinary skill in the art will appreciate that other methods employing materials having antibacterial properties may be used.

In use of the invention embodiment of FIGS. 15-24, a woman assembles the valve body 252 and valve cap 254 as described above and as shown in FIGS. 16 and 18, with flap valve 256 attached to valve cap 254 and covering opening 264b. One end of the suction hose 265 is firmly inserted into channel 263 of the valve body 252 through port 262. Next, the valve body, valve cap, valve flap and suction hose are assembled as described above, and the valve assembly 250 is placed axially over second end 219 of the adaptor 216 to form a seal between valve body 252 and second end 219 of the adaptor. As set forth above, the valve body, valve cap, flap valve and adaptor are all correctly rotationally aligned when assembled. Reservoir 218 is then positioned adjacent the adaptor 216 with second end 219 of adaptor 216, valve body 252, valve cap 254 and flap valve 256 all assembled and located in the interior volume 230 of reservoir 218 (FIG. 16). Reservoir 218 is rotated relative to adaptor 216 until slot 275 in upper lip 242 of the reservoir is aligned with notch 277 formed in lip 240 of adaptor 216 (FIG. 22). Suction hose 265 is laterally inserted into slot 275, and the reservoir 218 is then brought into contact with adaptor 216. Using hand pressure, snap fitting bump 243 of reservoir 218 is inserted into corresponding cradle 248 in adaptor 216 to maintain the adaptor in releasable contact with the reservoir 218. Except for the juxtaposition of slot 275 and notch 277 (FIG. 22), the engagement of snap fitting bump 243 with cradle 248 creates a seal between the adaptor 216 and reservoir 218 that prevents expressed milk from leaking from the reservoir. In use, the slot 275, notch 277 and suction hose 265 are located at the uppermost position of the device 200 to prevent the escape of expressed milk. The slot 275 also provides a vent to prevent the buildup of pressure in the reservoir 218, and provides a pouring opening when transferring milk from the reservoir to another container.

The other end of suction hose 265 is connected to an alternating suction pump (not shown), or to a connection device 270 (FIG. 23) that is connected to a hose 272 extending from an alternating suction pump. The woman then places her breast inside the breast adaptor 216, and places the device 200 within her brassiere to hold the device 200 in place so that she can utilize the device in a hands free manner. The user then activates the external pump, or other suction source, thus creating an alternating suction/positive pressure in hose 265. The flap valve 256 in the valve assembly 250, during the negative pressure cycle of the pump, encloses the space within the second end 219 of the breast adaptor 216, the valve assembly 250, and the suction line 265. During the negative or suction pressure cycle, the flap valve 256 is pulled tightly over the opening 264 in the valve cap 254 of the valve assembly 250 to create the reduced enclosed space which causes the breast to be drawn into the second end 219 of the breast adaptor 216 and release milk. After a period of time, if the expression of milk is rapid and voluminous, the expressed milk may fill up the second end 219 of the breast adaptor 216 and then flow through opening 251 and into the overflow chamber 258 during a single cycle. During the positive pressure cycle of the pump, the flap valve 256 opens and allows expressed milk to flow through the opening 264b in the end of the valve cap 254 and into the interior volume 230 of reservoir 218. During the ensuing negative or suction cycle of the pump, the flap valve 256 is again forced into contact with the valve cap and then tightly held against opening 264b to create the same reduced enclosure volume that applies suction directly to the breast, irrespective of the changing volume of air within the collection volume 230, which has been separated from the negative pressure volume. This cycle of operation is repeated until the woman decides that the expression of milk for that time period has concluded. Milk may then be transferred from the reservoir 218 into a suitable container for use at a later time. After use of the breast milk collection device 200, the various parts of the device are disassembled, thoroughly cleaned and decontaminated by hand washing, use of a dishwasher, steam sterilizer or the like, and then re-assembled as described above. It is contemplated that the various parts of the collection device 200 will be made from dishwasher safe materials and alternative materials can be adapted for specialized hospital applications.

The illustrated embodiment as shown in FIGS. 15-24 further allows a woman to pump one or both breasts in a variety of positions such as lying down, sitting upright, standing, or the like. Pumping while lying down, for example, will allow a woman to safely rest, or hold her infant while she is pumping, and possibly provide a woman the flexibility and convenience to easily breast feed her baby for a longer period of time in the child's life, by pumping whenever necessary to maintain her milk supply, which will diminish or cease altogether if pumping and/or breastfeeding are not performed on a several times daily and regular basis. In the illustrated embodiment, the circular ergonomic shape of the breast adaptor 216 and the milk reservoir 218 make pumping in a variety of positions feasible.

Figure 27:
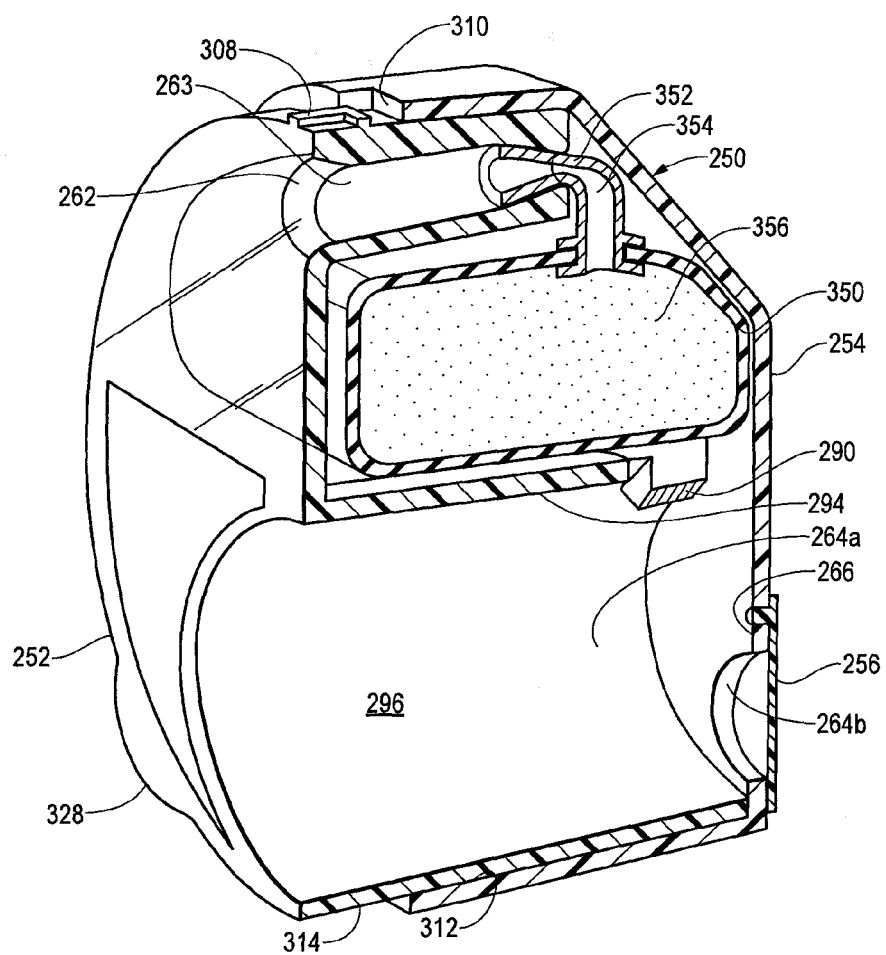
FIG. 27 is a front perspective partially cut-away embodiment of the tubing fitting for the vacuum hose connection apparatus for the embodiment of the invention shown in FIGS. 15 and 23, including the placement of a filter in the connection apparatus.

In an additional embodiment of the present invention disclose in FIG. 27, the vacuum source is physically isolated from the flow path of the expressed milk, totally preventing milk from entering and possibly contaminating the vacuum pump mechanism or the vacuum source line 265 (FIG. 16). FIG. 27 discloses the value body 252 and valve cap 254 of the embodiment of FIGS. 15 to 25, with pertinent modifications, and like numerals identify like parts. In this embodiment, baffle 260 (FIGS. 16, 20) is removed from valve cap 254. A barrier comprising a collapsible hollow bladder 350 is located in overflow chamber 258, and in the illustrated embodiment of FIG. 27, occupies a substantial portion of the volume of overflow chamber 258 when expanded. Bladder 350 includes a tubular neck 352 having a hollow portion 354 at one end that communicates directly with the interior 356 of bladder 350. Neck 352 at another end is tightly inserted into one end of channel 263, while vacuum source tube 265 is inserted in the other end of channel 263. The exterior surfaces of neck 352 and vacuum tube 265 tightly fit into their respective ends of channel 263, forming an air and fluid tight seal with channel 263 and port 262, and pneumatically connecting hollow portion 356 of bladder 350 to the source of vacuum pressure. In this manner, the vacuum pressure source conveyed through tube 265 is isolated from contact with overflow chamber 258, preventing milk that may enter chamber 258 from contacting or entering vacuum tube 265 or the pump supplying the vacuum source.

The collapsible bladder 350 may be formed in one piece, or more than one piece, from materials such as silicone, latex, or other such flexible materials, as are known to those of ordinary skill in the art. The volume of the interior 356 of collapsible bladder 350 is dimensioned sufficiently to transmit vacuum, or negative, pressure to the breast from the vacuum source, while applying sufficient oscillations on the breast to result in milk expression.

In use of the embodiment of FIG. 27, the vacuum source first creates a negative pressure through tube 265 and in hollow portion 356, causing bladder 350 to collapse. This creates a negative pressure in the interior of overflow chamber 258, with flap valve 256 in the closed portion over aperture 264. This negative pressure is conveyed through aperture 251 into passageway 296, and is applied to the breast and nipple, thereby drawing the breast and nipple into passageway 296. Milk is then expressed into passageway 296. Upon the release of negative pressure from the interior 356 of bladder 350, by the application of a pressure in excess of vacuum pressure, such as a positive pressure through tube 265 or by the application of a lesser negative pressure or a neutral pressure in tube 265 by releasing the vacuum pressure through a relief valve, bladder 350 expands to its full volume position, applying a positive pressure in overflow chamber 258, opening flap valve 256 and the milk is released through aperture 264b into reservoir 218 as previously described. As seen in FIG. 27, if there is an expression of a large volume of milk and a portion of the milk enters overflow chamber 258 through large aperture 251, the milk will be prevented by bladder 350, and the seal between tubular neck 352 and channel 263, from entering port 262, vacuum tube 265, or the pump mechanism providing the source of vacuum pressure. Thus, the possibility of contamination of vacuum tube 265 or of the source of vacuum pressure is eliminated.

For cleaning purposes, after the reservoir 218 has been removed from adaptor 216, valve cap 254 is removed from valve body 252, providing access to overflow chamber 258 and bladder 350. Neck 352 is manually removed from channel 263 and bladder 350 is removed from overflow chamber 258. Bladder 350 can then be washed manually or mechanically along with the other disassembled components of device 200.

Figure 25:
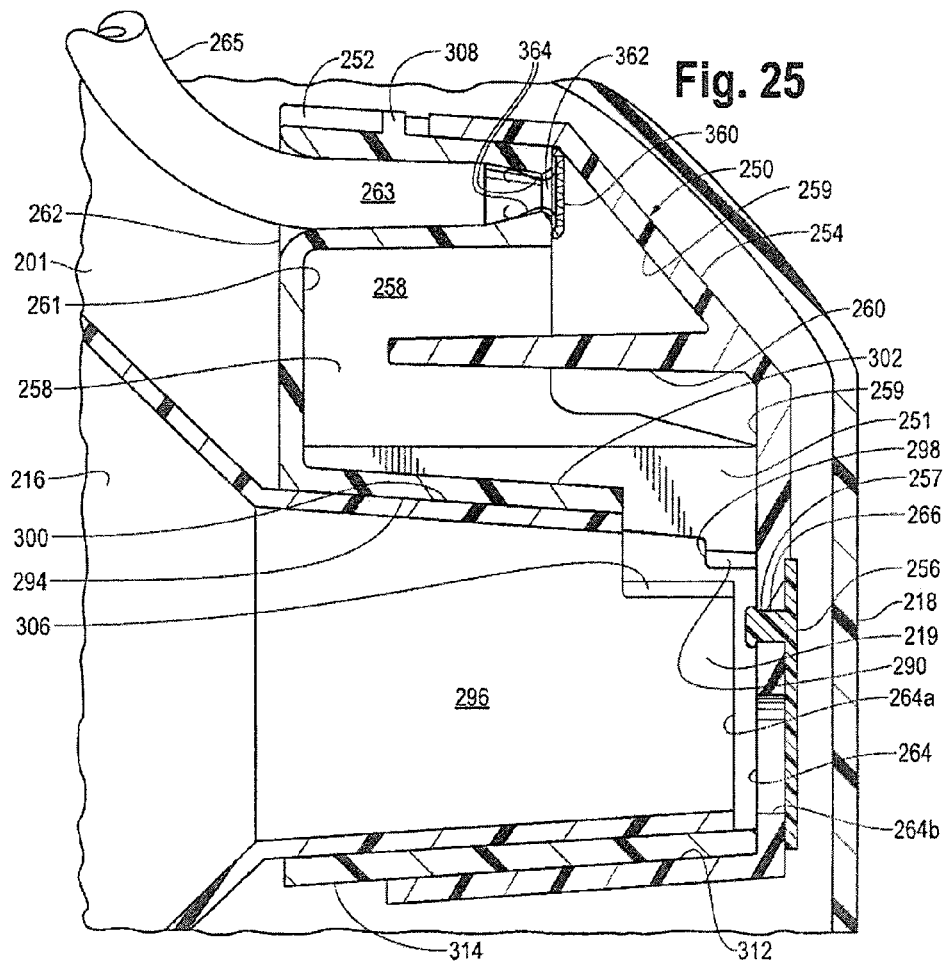
FIG. 25 is a perspective cross-sectional assembled view of the valve and valve cap of the present invention, showing an embodiment comprising a collapsible bladder isolating the path of breast milk flow from the source of vacuum pressure.

In a further embodiment of the present invention as disclosed in FIG. 25, a filter 360 is disposed adjacent opening 362 of channel 263. A resident single cage-like prong, or multiple spring prongs 364 are attached to one side of filter 360. Prongs 364 are adapted to extend into channel 263 through opening 362 and hold filter 360 in sealing engagement with opening 362.

Filter 360 is configured to allow air to pass from vacuum tube 265 and channel 263 through the filter 360 and into overflow chamber 258 and into passageway 296 during a negative pressure portion of the vacuum pressure cycle described previously. However, filter 360 is also configured to prevent the flow of expressed milk in the direction from overflow chamber 258 to vacuum source tube 265, thus preventing the flow of milk into tube 265 or to the pump providing the source of vacuum pressure.

Prongs 364 comprise outwardly extending tension springs that tightly engage the inner surface of channel 263, as seen in FIG. 25. The tension force applied by prongs 364 is sufficient to prevent filter 360 from becoming dislodged from channel 263 during repeated cycles of negative and positive pressure being applied through channel 263. Yet, the tension force applied by prongs 364 allows a user to manually remove the filter 360 from opening 362 for cleaning or for replacement.

Figure 26:
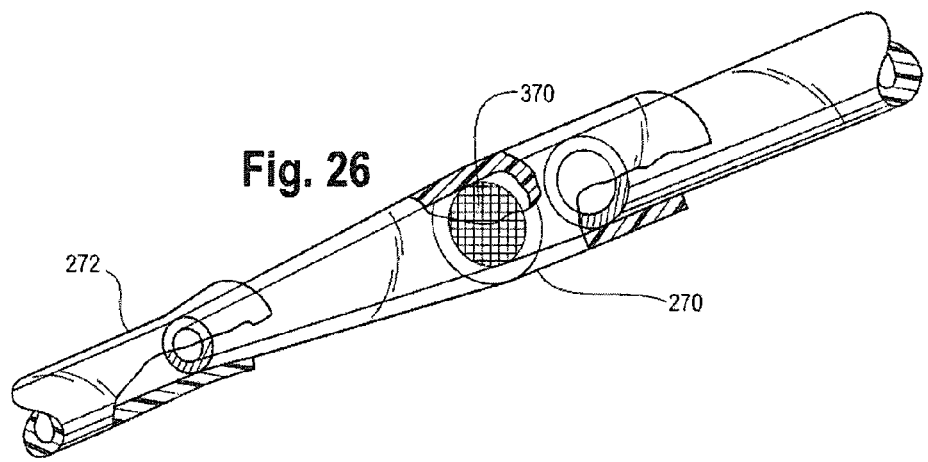
FIG. 26 is a cross sectional assembled view of a portion of the breast adaptor, the valve and the valve cap, showing an embodiment with a filter located between the overflow chamber and the source of vacuum pressure.

In a further embodiment illustrated in FIG. 26, connection apparatus 270 (FIG. 23) may be constructed with a filter 370, similar to the filter 360 described in conjunction with FIG. 25, inserted in channel 273. The filter 370 in channel 273 will be configured to allow positive, negative or neutral pressure air to pass between the source of vacuum pressure and channel 263 (FIG. 18), but the filter 370 will not allow milk to pass through the filter in the opposite direction through connection apparatus 270. Since connection apparatus 270 is a relatively inexpensive part of the invention described herein, if the filter 370 becomes clogged with milk, connection apparatus 270 may be discarded and replaced with a new connection apparatus and filter apparatus.

Figure 24:
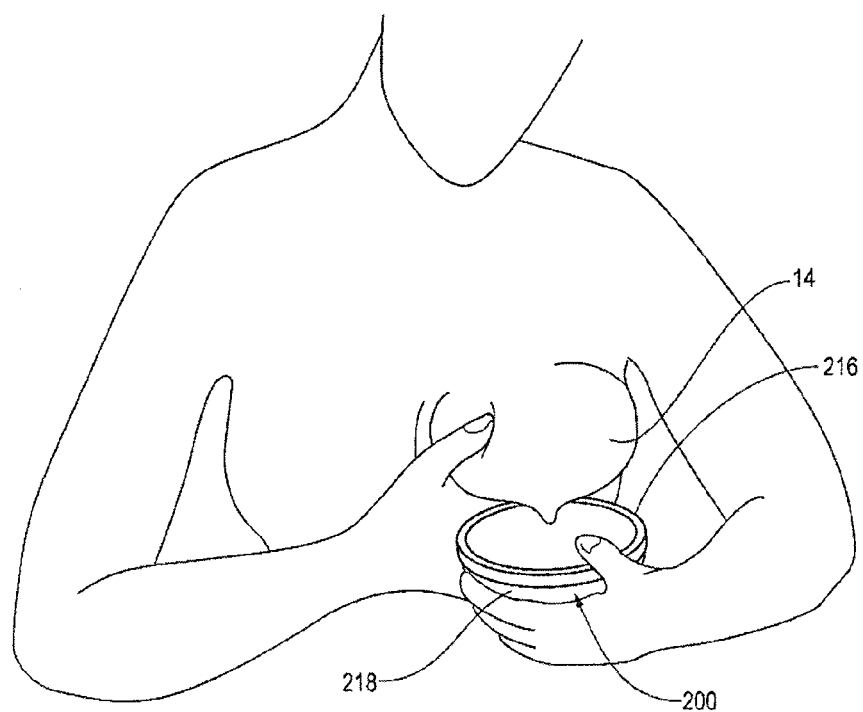
FIG. 24 is a front view of a woman's torso showing the present invention of FIG. 15 manually held under a woman's breast for use during hand expression of milk.

The collection device 200 of the illustrated embodiment in FIGS. 15-27 is multi-faceted. In addition to use with manual and electromechanical pumps and use for passive collection of breast milk, the device 200 can also be used as a collection device for hand expression of milk before, during, or after pumping. The collection device 200 can be used for collection of breast milk via hand expression while the device is held by hand as illustrated in FIG. 24, or placed on a table top with flat end 222 of reservoir 218 facing down, for example. By providing a wide opening to easily collect milk, either the first end 217 of the adaptor 216 when assembled on the collection device 200, or the reservoir 218 used alone allows a woman to lean over the device 200 while she is hand-expressing milk. Gravity will allow milk from a user's breast 14 to fall into the device 200 with a minimum of spillage and loss. The flap valve 256 is soft enough to allow expressed milk to flow from valve body passageway 296, through openings 264a and 264b, past valve 256 and into reservoir 218. The collection device 200 further allows a woman to follow up the pumping process with the recommended hand expression and massage techniques with a minimum of additional machines, hardware, and utensils to manage and clean. In an example, a woman may use the collection device 200 to pump breast milk hands-free, and after pumping, remove the device and place it flat on a nearby table or other flat surface, and continue expressing the remainder of milk by hand into the collection device 200.

A user may choose to remove the lid or adaptor 216 and use the reservoir 218 alone to collect hand-expressed milk. Additionally, a woman may choose to leave the device 200 fully assembled, and the funnel shape of the adaptor 216 will provide a large diameter area to collect milk and induce the milk via gravity to flow down through the adaptor 216 into the collection area or reservoir 218. This latter method reduces the risk of spillage or loss for expressed milk in the reservoir 218. After hand-expression is complete, a user may transfer the milk to a baby bottle or other storage device as previously described.

Finally, although the description above contains many specificities, these should not be construed as limiting the scope of the invention but as merely providing illustrations of some of the presently illustrated embodiments of this invention. This invention may be altered and rearranged in numerous ways by one skilled in the art without departing from the coverage of any patent claims which are supported by this specification.

What is claimed is:

1. A breast milk collection device comprising:
a breast adaptor having a first receiving end adapted to fittingly and sealingly receive at least a portion of a woman's breast, the adaptor having a second end opposite the first end, the second end including a first aperture adapted to receive a nipple portion of the breast;
a reservoir coupled with and enclosing the adaptor to form a single unit with the adaptor, an interior volume of the reservoir adapted to receive breast milk produced from the woman's breast in said breast adaptor through the first aperture of the second end of the adaptor, the interior volume of the reservoir adapted to store the milk within a brassiere worn by a woman, the reservoir adapted to be supported by the brassiere;
a valve assembly disposed between and surrounded by the adaptor and the reservoir, the valve assembly alternately opening and closing fluid communication between the adaptor and the reservoir, and
the valve assembly creating a reduced volume in communication with said second end of said adapter, said reduced volume being less than said interior volume of said reservoir.

2. The device of claim 1 wherein the reservoir is removably coupled with the adapter.

3. The device of claim 1, wherein said valve assembly is concentrically mounted on the second end of the adaptor.

4. The device of claim 1, further comprising an external suction source, said external suction source adapted to provide suction force to an interior portion of said device, said suction force adapted to facilitate the flow of breast milk from the woman's breast, the external suction source releasably connected to the collection device.

5. The device of claim 4, wherein said external suction source is an electric pump.

6. The device of claim 4, wherein said external suction source is a manually operated pump.

7. The device of claim 4 wherein a vacuum hose releasably connects the external suction source to the collection device.

8. The device of claim 1 including an external suction source applying a suction force to said reduced volume.

9. The device of claim 1 wherein said suction force is isolated from being applied to said interior volume of said reservoir.

10. The device of claim 1 wherein the flap valve closing the passage creates said reduced volume within the second end of the breast adaptor, the reduced volume becoming a negative pressure volume upon introducing suction to the reduced volume.

11. The device of claim 1 wherein said valve assembly includes a valve body mounted on said second end of said adaptor; and an overflow chamber formed in said valve body, said overflow chamber in fluid communication with a fluid passage formed in said second end of said adaptor.

12. The device of claim 11, wherein said valve body is removably mounted on said second end of said adaptor.

13. The device of claim 11 wherein said second end of said adaptor includes a second aperture and said valve body includes a third aperture communicating with said overflow chamber, said second and third apertures being aligned and providing said fluid communication between said fluid passage in said second end of said adaptor and said overflow chamber.

14. The device of claim 11 wherein said overflow chamber is adapted to receive breast milk from said second end of said adaptor upon the release of a volume of breast milk in excess of the capacity of the fluid passage formed in the second end of the adaptor.

15. The device of claim 11 wherein said valve body includes a first opening in communication with said overflow chamber, said first opening also communicating with a source of vacuum pressure, said vacuum pressure applied to said overflow chamber and to said fluid passage formed in said second end of said adaptor.

16. The device of claim 15, including a channel formed in said valve body, said first opening formed at a first end of said channel, a second end of said channel having a second opening communicating with said overflow chamber, said first opening releasably receiving a vacuum hose, said vacuum hose connected to said source of vacuum pressure.

17. The device of claim 11, including a valve cap sealingly mounted on said valve body, said valve cap including a baffle structure extending partially into said overflow chamber when said valve cap is mounted on said valve body.

18. The device of claim 17, said overflow chamber being operatively connected to a source of vacuum pressure, said baffle providing a torturous path for the vacuum pressure applied through the overflow chamber to the fluid passage formed in the second end of said adaptor.

19. The device of claim 18 wherein said baffle is adapted to impact breast milk entering said overflow chamber from said fluid passage of said second end of said adaptor and prevent the backflow of breast milk into said source of vacuum pressure.

20. The device of claim 1, wherein:
said reservoir includes a lip portion defining a rim of said reservoir, a slot formed in said lip portion, said slot extending from the exterior of said reservoir to said interior volume of said reservoir;
said adaptor having a flange portion adapted to removably engage said lip portion of said reservoir, a notch in said flange portion, said notch aligned with said slot in said reservoir when said reservoir and said adaptor are engaged.

21. The device of claim 20, wherein said notch and said slot, when aligned, form an access aperture in said adaptor and said reservoir, said access aperture extending between the interior volume of said reservoir and the exterior of said reservoir.

22. The device of claim 21, wherein said access aperture is adapted to receive a vacuum source hose, said vacuum source hose removably connected at one end to said valve assembly and at a second end to a source of vacuum pressure.

23. The device of claim 21, wherein said access aperture provides a vent for the escape of air during the receipt of breast milk by said reservoir.

24. The device of claim 1, further including:
a source of vacuum pressure;
a first flexible tubular vacuum hose connected to said source of vacuum pressure, said first vacuum hose having an inner diameter of a first dimension;
a second flexible tubular vacuum hose removably connected to said valve assembly, said second vacuum hose having an outer diameter of a second dimension;
a connection apparatus adapted to removably and replaceably connect said second vacuum hose to said first vacuum hose forming a vacuum force passageway between said source of vacuum pressure and said valve assembly;
said connector apparatus having a bore extending axially through said connector apparatus, said bore having an inner diameter adapted to sealingly receive one of said first and second flexible vacuum hoses.

25. The device of claim 24, wherein said connector apparatus has a tapered outer portion adapted to be sealingly received by the other of said first and second flexible tubular vacuum hoses.

26. The device of claim 1, wherein said valve assembly includes a second volume;
a hollow flexible bladder located in said second volume, the interior of said hollow flexible bladder in communication with a source of alternating vacuum pressure and pressure in excess of vacuum pressure, said hollow flexible bladder contracting in said second volume upon application of said vacuum pressure to said interior of said hollow flexible bladder, the contraction of said hollow flexible bladder creating a vacuum pressure in said second volume.

27. The device of claim 26 wherein said second volume is in communication with a passageway disposed in said second end of said adaptor, said vacuum pressure in said second volume adapted to facilitate the flow of breast milk from the woman's breast into said passageway when the breast is inserted in the first end of said adaptor.

28. The device of claim 27 wherein said second volume is less than said interior volume of said reservoir.

29. The device of claim 27 wherein said second volume is isolated from said interior volume of said reservoir when said vacuum pressure is created in said second volume.

30. The device of claim 29 wherein said second volume is in fluid communication with said interior volume of said reservoir when said pressure in excess of vacuum is introduced into said second volume.

31. The device of claim 1 wherein a second volume is formed in said valve assembly,
said valve assembly including an opening extending between a source of vacuum pressure and said second volume;
said second volume being less than said interior volume of said reservoir;
said valve assembly including a valve alternately opening and closing communication between said adaptor and said reservoir;
a hollow flexible bladder located in said second volume, the interior of said hollow flexible bladder in sealing communication with a source of alternating vacuum pressure and pressure in excess of vacuum pressure, said hollow flexible bladder contracting in said second volume when vacuum pressure is applied to the interior of said hollow flexible bladder, said vacuum pressure being applied in said second volume when said bladder contracts.

32. The device of claim 31 wherein said flexible bladder expands upon application of said pressure in excess of vacuum pressure to the interior of said hollow flexible bladder, the pressure in said second volume being increased upon said expansion of said bladder.

33. The device of claim 32 wherein said valve opens communication between said adaptor and said reservoir when the pressure in said second volume is in excess of vacuum pressure.

34. The device of claim 26 wherein the interior of said hollow flexible bladder is sealed against fluid communication with said second volume.

35. The device of claim 1 wherein said valve assembly includes a valve body removably and concentrically mounted on said second end of said adaptor;
a passageway extending through said second end of said adaptor, said passageway including an opening portion adjacent an edge of said second end of said adaptor;
said valve body including a chamber sealingly receiving the second end of said adaptor upon mounting said valve body on said second end of the adaptor, said chamber including at least one projection extending partially into said chamber of said valve body, said at least one projection advancing into said opening portion of said adaptor only when said valve body is correctly circumferentially oriented with said adaptor.

36. The device of claim 35 wherein said at least one projection comprises two projections, each projection engaging a sidewall of said opening when said valve body is correctly mounted on said second end of said adaptor.

37. The device of claim 35, wherein said second end of said adaptor has a tapered outer surface, and said chamber in said valve body has a tapered inner surface, said tapered inner and outer surfaces forming a fluid tight seal between said second end of said adaptor and said chamber when said valve body chamber is mounted on said tapered surface of said second end of said adaptor and said at least one projection advances into said opening.

38. The device of claim 35, wherein said at least one projection abuts said edge of the second end of said adaptor when said valve body is incorrectly circumferentially oriented with said second end of said adaptor, preventing the advance of said at least one projection into said opening.

39. The device of claim 1 wherein said valve assembly includes a valve body having an outer circumferential surface;

said valve assembly further including a valve cap having a circumferential inner surface portion, said circumferential inner surface portion removably and sealingly mounted on the outer circumferential surface of said valve body;

said outer circumferential surface of said valve body comprising a key located at a predetermined location on said outer surface;

said circumferential inner surface of said valve cap comprising a keyway slot, said keyway slot receiving said key when said valve body and said valve cap are correctly concentrically oriented.

40. The device of claim 1 wherein said adaptor, said reservoir, said valve body, said valve cap and said flap valve are all manually removable respectively from each other, providing ease of cleaning of each element of the device.

41. The device of claim 4 wherein said valve assembly includes a first flow path adapted to substantially linearly advance said breast milk to said reservoir, said first flow path defining a first axis;

said external suction source providing said suction force to said valve assembly along a second axis;

said first and second axes being spaced apart in said valve assembly.

* * * * *